United States Patent [19]

Yeh et al.

[11] Patent Number: 5,258,292

[45] Date of Patent: Nov. 2, 1993

[54] ENZYMIC PROCESS FOR THE SYNTHESIS OF AMMONIUM ADIPATE

[75] Inventors: Patrice Yeh, Paris; Jean-Francois Mayaux, Fontenay aux Roses; Edith Cerbelaud; Dominique Petre, both of Lyons, all of France

[73] Assignee: Rhone-Poulenc Chimie, Courbevoie, France

[21] Appl. No.: 796,361

[22] Filed: Nov. 22, 1991

[30] Foreign Application Priority Data

Nov. 28, 1990 [FR] France .................................. 90 14853

[51] Int. Cl.$^5$ .......................... C12P 13/00; C12P 7/62; C12N 9/80
[52] U.S. Cl. .................................... 435/128; 435/135; 435/174; 435/228
[58] Field of Search ................ 435/128, 135, 228, 174

[56] References Cited

PUBLICATIONS

Soubrier, F., et al. (1992) Gene 116, 99-104.
Maestracci et al. (1986) Microbiologie Aliments Nutrition 4 19-24.
Suggs, S. Vi, et al, (1981) Proc. Natl. Acad. Sci, U.S.A. 78(11), 6613-6617.

*Primary Examiner*—Charles L. Patterson, Jr.
*Attorney, Agent, or Firm*—Burns, Doane, Swecker & Mathis

[57] ABSTRACT

The invention relates to an enzymic process for the synthesis of ammonium adipate by the hydrolysis of adipamide and/or ammonium adipamate by means of a particular polypeptide or a recombinant microorganism generating this polypeptide.

6 Claims, 25 Drawing Sheets

| PURIFICATION STEP | VOLUME (ml) | AMOUNT OF PROTEIN (mg) | ACTIVITY (U/mg) | YIELD (%) | PURIFICATION |
|---|---|---|---|---|---|
| 1) CRUDE EXTRACT | 325 | 1918 | 26.4 | 100 | 1 |
| 2) PRECIPITATE AMMONIUM SULFATE | 29.5 | 613 | 62.5 | 75 | 2.4 |
| 3) ELUATE PHENYL-SEPHAROSE | 77 | 200 | 198 | 78 | 7.5 |
| 4) FIRST ELUATE AcA 44 | 6 | 27 | 457 | 24.4 | 17.3 |
| 5) SECOND ELUATE AcA 44 | 3 | 3.9 | 815 | 6.3 | 31 |

FIG.1

N-terminal end

ATIRPDDKAIDAAARHYGITLDKTA (R)L...

Internal Fragment

-LEVPALI (D) GALGSYDVVDQLY...

```
5'                              3'
 I  D  G  A  L  G  S  Y  D  V
ATCGATGGCGCCCTCGGCTCCTACGATGT       CODING STRAND
   T  C  T  A  G  T  T  T  C
               G
               T
II II II II  I II   II II II        EXACT POSITIONS
100100 88100 57 88 62100100
                                    TOTAL FREQUENCIES (%)
3'                              5'
TAGCTGCCGCGGGAGCCGAGGATGCTGCA       PROBE (Sg 762)
         C  C
         T
```

FIG.2

```
        A      T AT
48°C           T AT
        C      T
        A      T A
               T AA
    ---------------------
        C  ( ) G T
        A      T T
45°C           T
               C
        C C A C T
                        GATGCCGTAATGCCTTGCGGCGGCGTCTATTGCTTTGTC
5' AAGCTT GCTGTTTTGTCAAGCGT
3'        CGACAAAACAGTTCGCA
                        CTACGGCATTACGGAACGCCGCCGCAGATAACGAAACAG
     ThrLysAspLeuThrIleGlyTyrHisArgAlaAlaAlaAspIleAlaLysAsp
                                            ←-----

G A    T
        G A G C G
48°C    G A
        G   G
        G G
    ---------------------
        G G    C
        A      G
45°C    G    A
        A C  CTAAG
        A G G

GTCTGGTCGAATGGTATC        3'
CAGACCAGCTTACCATAGCTTAAG  5'
AspProArgIleThrAsp
```

FIG.3A

```
5'                                              3'
  GATGCGGTAATGCCTTGCGGCGGCGTCTATTGCTTTGTCG    Exact probe (Sq 918)
```

FIG.3B

Seq.ID NO.11  cgatccggaaacagtacttcggcagcttgccacgacaccgaaaagctctacgaacaccggtgttccactgca  72 tcggccgattctgatcgctgaatcggcccgtgggcgactgtaccccccgctctctctgagcgcacgtaacccg  144

BamHI aacttaacgagtcaatatgtcgatacctattgacgcaattatggatccggccctagtctgaaagacaagtga  216
     SD                                   amidase agccgatcacatcaggagcacacttctc ATG GCG ACA ATC CGA CCT GAC GAC AAA GCA ATA  277
Seq.ID NO.11                         Met Ala Thr Ile Arg Pro Asp Asp Lys Ala Ile  11

GAC GCC GCC GCA AGG CAT TAC GGC ATC ACT CTC GAC AAA ACA GCC CGG CTC GAG  331
Asp Ala Ala Ala Arg His Tyr Gly Ile Thr Leu Asp Lys Thr Ala Arg Leu Glu  29

TGG CCG GCA CTG ATC GAC GGA GCA CTG GGC TCC TAC GAC GTC GTC GAC CAG TTG  385
Trp Pro Ala Leu Ile Asp Gly Ala Leu Gly Ser Tyr Asp Val Val Asp Gln Leu  47

TAC GCC GAC GAG GCG ACC CCG CCG ACC ACG TCA CGC GAG CAC GCG GTG CCA AGT  439
Tyr Ala Asp Glu Ala Thr Pro Pro Thr Thr Ser Arg Glu His Ala Val Pro Ser  65

GCG AGC GAA AAT CCT TTG AGC GCT TGG TAT GTG ACC ACC AGC ATC CCG CCG ACG  493
Ala Ser Glu Asn Pro Leu Ser Ala Trp Tyr Val Thr Thr Ser Ile Pro Pro Thr  83

TCG GAC GGC GTC CTG ACC GGC CGA CGC GTG GCG ATC AAG GAC AAC GTG ACC GTG  547
Ser Asp Gly Val Leu Thr Gly Arg Arg Val Ala Ile Lys Asp Asn Val Thr Val  101

GCC GGA GTT CCG ATG ATG AAC GGA TCT CGG ACG GTA GAG GGA TTT ACT CCG TCA  601
Ala Gly Val Pro Met Met Asn Gly Ser Arg Thr Val Glu Gly Phe Thr Pro Ser  119

CGC GAC GCG ACT GTG GTC ACT CGA CTA CTG GCG GCC GGT GCA ACC GTC GCG GGC  655
Arg Asp Ala Thr Val Val Thr Arg Leu Leu Ala Ala Gly Ala Thr Val Ala Gly  137

AAA GCT GTG TGT GAG GAC CTG TGT TTC TCC GGT TCG AGC TTC ACA CCG GCA AGC  709
Lys Ala Val Cys Glu Asp Leu Cys Phe Ser Gly Ser Ser Phe Thr Pro Ala Ser  155

GGA CCG GTC CGC AAT CCA TGG GAC CGG CAG CGC GAA GCA GGT GGA TCA TCC GGC  763
Gly Pro Val Arg Asn Pro Trp Asp Arg Gln Arg Glu Ala Gly Gly Ser Ser Gly  173

FIG.9A

```
GGC AGT GCA GCA CTC GTC GCA AAC GGT GAC GTC GAT TTT GCC ATC GGC GGG GAT  817
Gly Ser Ala Ala Leu Val Ala Asn Gly Asp Val Asp Phe Ala Ile Gly Gly Asp  191

CAA GGC GGA TCG ATC CGG ATC CCG GCG GCA TTC TGC GGC GTC GTC GGG CAC AAG  871
Gln Gly Gly Ser Ile Arg Ile Pro Ala Ala Phe Cys Gly Val Val Gly His Lys  209

CCG ACG TTC GGG CTC GTC CCG TAT ACC GGT GCA TTT CCC ATC GAG CGA ACA ATC  925
Pro Thr Phe Gly Leu Val Pro Tyr Thr Gly Ala Phe Pro Ile Glu Arg Thr Ile  227

GAC CAT CTC GGC CCG ATC ACA CGC ACG GTC CAC GAT GCA GCA CTG ATG CTC TCG  979
Asp His Leu Gly Pro Ile Thr Arg Thr Val His Asp Ala Ala Leu Met Leu Ser  245

GTC ATC GCC GGC CGC GAC GGT AAC GAC CCA CGC CAA GCC GAC AGT GTC GAA GCA  1033
Val Ile Ala Gly Arg Asp Gly Asn Asp Pro Arg Gln Ala Asp Ser Val Glu Ala  263

GGT GAC TAT CTG TCC ACC CTC GAC TCC GAT GTG GAC GGC CTG CGA ATC GGA ATC  1087
Gly Asp Tyr Leu Ser Thr Leu Asp Ser Asp Val Asp Gly Leu Arg Ile Gly Ile  281

GTT CGA GAG GGA TTC GGG CAC GCG GTC TCA CAG CCC GAG GTC GAC GAC GCA GTC  1141
Val Arg Glu Gly Phe Gly His Ala Val Ser Gln Pro Glu Val Asp Asp Ala Val  299

CGC GCA GCG GCA CAC AGT CTG ACC GAA ATC GGT TGC ACG GTA GAG GAA GTA AAC  1195
Arg Ala Ala Ala His Ser Leu Thr Glu Ile Gly Cys Thr Val Glu Glu Val Asn  317
                        Sph I
ATC CCG TGG CAT CTG CAT GCT TTC CAC ATC TGG AAC GTG ATC GCC ACG GAC GGT  1249
Ile Pro Trp His Leu His Ala Phe His Ile Trp Asn Val Ile Ala Thr Asp Gly  335

GGT GCC TAC CAG ATG TTG GAC GGC AAC GGA TAC GGC ATG AAC GCC GAA GGT TTG  1303
Gly Ala Tyr Gln Met Leu Asp Gly Asn Gly Tyr Gly Met Asn Ala Glu Gly Leu  353

TAC GAT CCG GAA CTG ATG GCA CAC TTT GCT TCT CGA CGC ATT CAG CAC GCC GAC  1357
Tyr Asp Pro Glu Leu Met Ala His Phe Ala Ser Arg Arg Ile Gln His Ala Asp  371

GCT CTG TCC GAA ACC GTC AAA CTG GTG GCC CTG ACC GGC CAC CAC GGC ATC ACC  1411
Ala Leu Ser Glu Thr Val Lys Leu Val Ala Leu Thr Gly His His Gly Ile Thr  389
```

FIG.9B

```
ACC CTC GGC GGC GCG AGC TAC GGC AAA GCC CGG AAC CTC GTA CCG CTT GCC CGC  1465
Thr Leu Gly Gly Ala Ser Tyr Gly Lys Ala Arg Asn Leu Val Pro Leu Ala Arg   407

GCC GCC TAC GAC ACT GCC TTG AGA CAA TTC GAC GTC CTG GTG ATG CCA ACG CTG  1519
Ala Ala Tyr Asp Thr Ala Leu Arg Gln Phe Asp Val Leu Val Met Pro Thr Leu   425

CCC TAC GTC GCA TCC GAA TTG CCG GCG AAG GAC GTA GAT CGT GCA ACC TTC ATC  1573
Pro Tyr Val Ala Ser Glu Leu Pro Ala Lys Asp Val Asp Arg Ala Thr Phe Ile   443

ACC AAG GCT CTC GGG ATG ATC GCC AAC ACG GCA CCA TTC GAC GTG ACC GGA CAT  1627
Thr Lys Ala Leu Gly Met Ile Ala Asn Thr Ala Pro Phe Asp Val Thr Gly His   461

CCG TCC CTG TCC GTT CCG GCC GGC CTG GTG AAC GGG CTT CCG GTC GGA ATG ATG  1681
Pro Ser Leu Ser Val Pro Ala Gly Leu Val Asn Gly Leu Pro Val Gly Met Met   479

ATC ACC GGC AGA CAC TTC GAC GAT GCG ACA GTC CTT CGT GTC GGA CGC GCA TTC  1735
Ile Thr Gly Arg His Phe Asp Asp Ala Thr Val Leu Arg Val Gly Arg Ala Phe   497
         HindIII
GAA AAG CTT CGC GGC GCG TTT CCG ACG CCG GCC GAA CGC GCC TCC AAC TCT GCA  1789
Glu Lys Leu Arg Gly Ala Phe Pro Thr Pro Ala Glu Arg Ala Ser Asn Ser Ala   515

CCA CAA CTC AGC CCC GCC tagtcctgacgcactgtcagacaacaaattccaccgattcacacatg  1854
Pro Gln Leu Ser Pro Ala                                                    521 atcagcccacataagaaaaggtgaa
```

FIG.9C

|  |  |  |  |  |  |  |  |  |  |  |
|---|---|---|---|---|---|---|---|---|---|---|
| 1029 | 1752 | 1029 | 1752 | 1029 | 1751 | 906 | 1751 | 906 | 1751 | 906 PLASMID |
| 42° | 42° | 42° | 42° | 42° | + | − | + | − | + | − trp |

S: SUPERNATANT
T: TOTAL
C: PELLET
M: MARKER pxL 1029: IL1β UNDER THE CONTROL OF PRcIts
pxL 906:    "        "      "       "    Ptrp Seq ID No.12

PstI
ctgcagaacggaactaagatggctcgaaccttcaccaaagacggacttgaacacagcctcgcac 64
∿∿∿∿
ttgcgcgtttggagctcccggacgagcgttacgagacggtgacagcggctgccgagttggtcct 128 cggactcgctgaggctctggatgctgtcccgctggccgagactccgatggcagccgccttcgat 192

Seq ID No.13 gcgcggtgggagtgacg<span style="border:1px solid">atg</span> GGC TTG CAT GAA CTG ACG CTC GCG CAA GTC GCT 245
                           G   L   H   E   L   T   L   A   Q   V   A GCG AAG ATC GAG AAC AAA GAA CTT TCC CCG GTC GAG CTC CTC GAT GTG 293
 A    K    I    E    N    K    E    L    S    P    V    E    L    L    D    V ATC CTG GCG CGC GTC GCG GAG ATC GAA CCG AAG ATC TCC GCC TTC GTC 341
 I    L    A    R    V    A    E    I    E    P    K    I    S    A    F    V ACG ATC ACC GCC GAT TCC GCT CGG AAG GCG GCC CGG CTC GCA GCC GAC 389
 T    I    T    A    D    S    A    R    K    A    A    R    L    A    A    D GAG ATC GCA GGT GGG CAC TAT CGC GGT CCG CTG CAC GGA GTT CCG ATT 437
 E    I    A    G    G    H    Y    R    G    P    L    H    G    V    P    I GGC CTC AAG GAT CTG TTC GAA GTG GCA GGC GTC CCG AAT ACC GCG AGT 485
 G    L    K    D    L    F    E    V    A    G    V    P    N    T    A    S TCG CGG GTC CGA GCT GAC TAC ATC CCC TCA TCG GAT GGG GCC GCG GTC 533
 S    R    V    R    A    D    Y    I    P    S    S    D    G    A    A    V GAG AAG CTC ACC GCC GGT GGA GCG GTC ATG ATC GGC AAG ACG CAC ACT 581
 E    K    L    T    A    G    G    A    V    M    I    G    K    T    H    T CAC GAA TTC GCC TAC GGT GCG ATC ACA CCG ACC ACC CGT AAT CCA TGG 629
 H    E    F    A    Y    G    A    I    T    P    T    T    R    N    P    W GAC CCC ACC CGG ACA CCC GGC GGT TCC AGC GGT GGG ACG GCA GCA GCT 677
 D    P    T    R    T    P    G    G    S    S    G    G    T    A    A    A

FIG. 14A

```
CTC GCG GCA GGC CTC ATC TTC GCC GGT ATG GGT ACC GAT ACC GGG GGG    725
 L   A   A   G   L   I   F   A   G   M   G   T   D   T   G   G

TCC ATT CGG ATA CCA GCC GCC GTC TGC GGG ACG GTA GGT CTC AAA CCC    773
 S   I   R   I   P   A   A   V   C   G   T   V   G   L   K   P

ACA TAT GGT CGC GTT TCG CGT CGT GGA GTG ACC TCC TTG TCA TGG TCT    821
 T   Y   G   R   V   S   R   R   G   V   T   S   L   S   W   S

CTG GAC CAC GCG GGA CCG CTG GCC CGG ACC GTG GAA GAC GCT GCC ATC    869
 L   D   H   A   G   P   L   A   R   T   V   E   D   A   A   I

ATG CTG AAC CAG ATC GCT GGC TAT GAC CGG GCT GAT CCT GCG ACG GTA    917
 M   L   N   Q   I   A   G   Y   D   R   A   D   P   A   T   V   pep 123

GAT GTG CCC GTT CCC GAC TAC GCG GCG GCG CTG ACC GGA GAC GTC CGA    965
 D   V   P   V   P   D   Y   A   A   A   L   T   G   D   V   R

GGG CTG CGG ATT GGT GTG CCG ACC AAT TTC TAC ACC GAC AAC GTC CAT   1013
 G   L   R   I   G   V   P   T   N   F   Y   T   D   N   V   H

CCC GAG GTT GCC GCA GCG GCC GAC GCT GCG GTG GCG CAA CTG GCC CAT   1061
 P   E   V   A   A   A   A   D   A   A   V   A   Q   L   A   H

TTG GGT GCG GTG GTC CGC GAA GTG AAG ATC CCG ATG GCA GAG GTC ATC   1109
 L   G   A   V   V   R   E   V   K   I   P   M   A   E   V   I

GTG CCC ACC GAG TGG AGC TTG CTC GTC CCG GAG GCG TCG GCC TAC CAC   1157
 V   P   T   E   W   S   L   L   V   P   E   A   S   A   Y   H

CAG CAG ATG CTG CGC GAG CGC GCA GAT CAC TAC ACC GAC GAG ACG AGA   1205
 Q   Q   M   L   R   E   R   A   D   H   Y   T   D   E   T   R

ACC TTC CTG GAA GCC GGC GAA CTC GTT CCG GCG ACC GAC TAC ATC AAG   1253
 T   F   L   E   A   G   E   L   V   P   A   T   D   Y   I   K   pep 124
```

FIG. 14B

```
GCG CTG CGG GTG CGC ACC CTC ATC CAG GCA GCC TTC CGG GAA CTG TCC   1301
 A   L   R   V   R   T   L   I   Q   A   A   F   R   E   L   F

CAG GAC ATC GAT GTC CTG ATC GCA CCC ACG GTC AGC TCT CCG GCT CTG   1349
 Q   D   I   D   V   L   I   A   P   T   V   S   S   P   A   L   pep 162

CCG CTC GAT GAC CTG GAA GTC ACT TGG CCC GAT GGC ACA TCC GAA GGC   1397
 P   L   D   D   L   E   V   T   W   P   D   G   T   S   E   G

GGC ACC ATC ACC TAT GTC CGT CTC AGC GCC CCC GGC AAC GTC ACC GGA   1445
 G   T   I   T   Y   V   R   L   S   A   P   G   N   V   T   G

CTT CCA GCG CTG TCG GTC CCC TCC GGC TTC ACC GAG CAA GGC CTT CCC   1493
 L   P   A   L   S   V   P   S   G   F   T   E   Q   G   L   P

ACC GGT ATC CAG ATC ATC GGC CGT CCC TTC GAC GAG GAG ACC GTC CTC   1541
 T   G   I   Q   I   I   G   R   P   F   D   E   E   T   V   L

AAC GTC GGT CAC GCC TAC GAA GGC TGC ACG GAC TGG CCG CGA CTG GCG   1589
 N   V   G   H   A   Y   E   G   C   T   D   W   P   R   L   A

CCG CTT tgabctactgaccccattggagaaaaccgaaggagagaacgatg
 P   L                                         SalI
```

FIG.14C

Seq.ID NO.14        GGC GGT TCC AGC GGT GGG ACG GCA GCA GCT
Seq.ID NO.15         G   G   S   S   G   G   T   A   A   A

CTC GCG GCA GGC CTC ATC TTC GCC GGT ATG GGT ACC GAT ACC GGG GGG
 L   A   A   G   L   I   F   A   G   M   G   T   D   T   G   G

TCC ATT CGG ATA CCA GCC GCC GTC TGC GGG ACG GTA GGT CTC AAA CCC
 S   I   R   I   P   A   A   V   C   G   T   V   G   L   K   P

ACA TAT GGT CGC GTT TCG
 T   Y   G   R   V   S

FIG.15

```
         90        100       110       120       130       140       150
-DGVLTGRRVAIKDNVTVAGVPMMNGSRTVEGFTPSRDATVVTRLLAAGATVAGKAVCEDLCFSGSSFTP
 == =  = —=    ===  -=   - = =-- =  ==-== -  =-   - - :-- =
YRGPLHGVPIGLKDLFEVAGVPNTASSRVRADYIPSSDGAAVEKLTAGGAVMIGKTHTHFFAY-GA-ITP
   70        80        90        100       110       120       130
        160       170       180       190       200       210       220
ASGPVRNPWDRQREAGGSSGGSAALVANGDVDFA-IGGDQGGSIRIPAAFCGYVGHKPTFGLVPYTGAFP
 --   ===  =  ===== -=  -=  = -  =--==  =======  = = = =-== ==
TT---RNPWDPTRTPGGSSGGTAAALAAGLI-FAGMGTDTGGSIRIPAAYCGTVGLKPTYGRVSRRGVTS
       140       150       160       170       180       190       200
      230       240       250       260       270       280       290
IERTIDHLGPITRTVHDAALMLSVLAGRDGNDPRQADSVEAGDYLSTLDSDVDGLRIGIVREGFGHAVSQ
-  --==  =-=  ===   == =  ==    ==     =   =  -=  -=  ===  - --  =
LSWSLDHAGPLARTVEDAAIMLNQIAGYDRADPATVD-VPVPDYAAALTGDVRGLRIGVPTNFYTDNV-H
        210       220       230       240       250       260
    300       310       320       330       340       350
PEVDDAVRAAAHSLTEIGCTVEEVNIPW-HIHAFHIVNVIATDGGAY-Q-MLDGNGYGMNAEGLYDPELM
 ==  =  =- :- -=  === =    -     =-- ---== =   -    --
PEVAAAADAAVAQLAHLGAVVREVHIPMAIVIVPTEWSLLVPEASAYHQQMLRERA-DHYTDE--TRTFL
         280       290       300       310       320       330
```

FIG.16

```
            90        100       110       120       130             140
         AGVPNTASSRVRADYIPSSDGAAVEKLTAGGAYMIGKTHTHIFAYGAIT-P-T---TRNPWDPTRTPGGS
          -      -- -=    =- =---=-= =--=   == -   == - -=== -=- =
         NT-SSIKGMK-ESGYRADHDAYFVQRMRAAGFVLLGKVNTPEMGTQVTTEPEAVGATRNPWNLGRSVGGS
            90        100       110       120       130       140       150
                160       170       180       190       200       210
         SGGTAAALAAGLIFAGMGTDTGGSIRIPAAYCGTVGLKPTYGRYSRRG-VTSLSV-S-LDHAGPLARTVE
         ==-=-=-=   -=  =--=-=---=-= ====  ==-=  =     --  ==  =-=
         SGGSGAAVAAALSPVAHGNDAAGSVRIPASVCGVVGLKPTRGRISPGPLYTDSDNVAGAAHEGLFARSVR
                160      ·170       180       190       200       210       220
            220       230       240       250       260       270       280
         DAALMLNQLAGYDRADPATVDVPYPDYAAALTGDVRGLRIGVPTNF-YTD-NVHPEVAAAADAAVAQLAH
         ==  = -=-  -=    -=       =---- -=-= =   -= - ==== -==
         DIAALLDYVSGHRPGDTFCAPTASRPYAQGISENPGSLRYGVLTHNPVGDFALDPECAAAARGAAAALAA
                230       240       250       260       270       280       290
            290
         LGAVVREV
         ==  = -
         LGHDVNDA
```

FIG.17

P : PURIFIED AMIDASE

C : PELLET
T : TOTAL PROTEIN  } OF THE STRAIN OF E coli E103S (pXL1894)
S : SUPERNATANT

ENZYMIC PROCESS FOR THE SYNTHESIS OF AMMONIUM ADIPATE

The present invention relates to an enzymic process for the synthesis of ammonium adipate.

More precisely, the invention relates to a process for the synthesis of ammonium adipate by the hydrolysis of adipamide and/or ammonium adipamate by means of a specific enzymic catalyst.

It is known that ammonium adipate is a particularly valuable product because it can be converted to adipic acid, itself a product widely used for the preparation of nylon.

The synthesis of ammonium adipate by the enzymic hydrolysis of adipamide is already known in principle.

Thus, among the microorganisms for which it has been possible to demonstrate the existence of this enzymic activity, there may be mentioned more particularly the strains belonging to the genus *Brevibacterium*, and especially *Brevibacterium* R 312 (see in this connection ARNAUD et al., "Etude de activitá amidasique de quelques bactéries" ("Study of the amidase activity of some bacteria"), in Folia Microbiologica, 1976, 21. pages 178-185). Moreover, the existence within *Brevibacterium* of an amidase with socalled "general activity", which can be used directly for the bioconversion of amides to acid salts, and especially of adipamide to ammonium adipate, has also already been demonstrated (see in this connection MAESTRACCI et al. in Microbiologie Aliments-Nutrition, 1986, vol. 4, pages 19-24).

However, it is found that the enzymic activity of *Brevibacterium* R 312, or of its above-described amidase with general activity, is insufficient to permit a high and hence viable production of ammonium adipate from adipamide.

One of the objects of the present invention is therefore to provide an enzymic process for the synthesis of ammonium adipate which gives improved yields.

Now, it has been found by the Applicant that this object can be achieved by using suitably selected enzymes, either as such or, preferably, in the form of recombinant microorganisms generatinq said enzymes.

More precisely, a novel process for the synthesis of ammonium adipate by the hydrolysis of adipamide and/or ammonium adipamate by means of a polypeptide having an amidase activity, or a recombinant microorganism generating said polypeptide, is now proposed which comprises using:

(i) a polypeptide coded for by a DNA sequence selected from:
   the sequence coding for the amidase of *Brevibacterium* R 312, shown in FIG. 9,
   an analog of this sequence resulting from the degeneracy of the genetic code, and
   a DNA hybridizing with one of these sequences or with a fragment thereof and coding for a polypeptide having an amidase activity; or (ii) a recombinant microorganism generating said polypeptide.

In one particular embodiment of the invention, a polypeptide (or a recombinant microorganism generating this polypeptide) is used which is coded for by the sequence as shown in FIG. 14 or by a variant of this sequence. Variant is understood here as meaning any sequence which, despite a few degradations resulting for example from mutations, deletions or insertions, or else from the degeneracy of the genetic code, conserves the properties of the initial sequence.

As indicated below, such sequences can be found in strains of the *Rhodococcus* type.

According to the present invention, the DNA sequence shown in FIG. 14 is considered as hybridizing with the DNA sequence shown in FIG. 9.

The polypeptides as defined above, and the recombinant microorganisms generating these polypeptides, which are used in the process according to the present invention, have already been described in the French patent application filed under number 8916332 in the name of RHONE-POULENC SANTE. As such, they do not therefore form the subject of the present invention.

In very general terms, said patent application, which has not yet been published, relates to polypeptides possessing a so-called enantioselective amidase activity, to the DNA sequences permitting their expression, to a process for their preparation and to their use as catalysts for the enantioselective hydrolysis of racemic amides to an acid in either the S form or the R form. These polypeptides, and the genetic material permitting their expression, have all been obtained in accordance with the Examples which will be given below.

It will therefore be noted that the processes for the preparation of such polypeptides or the genetic material permitting their expression, or of the recombinant microorganisms generating said polypeptides, do not form the subject of the present invention.

The present invention is in fact based on the discovery that such polypeptides having an enantioselective amidase activity also have the remarkable property of being able to hydrolyze adipamide and/or ammonium adipamate to ammonium adipate with particularly high yields. The present invention therefore relates solely to a novel use of particular polypeptides.

Although French patent application 8916332 cited above is totally included here by way of reference, its content and its teachings will be at least partially redeveloped, especially as far as the Examples are concerned, for the purposes of the present disclosure.

The DNA sequences which code for the polypeptides used in the process according to the invention can be obtained in a variety of ways. The general strategy consists in using nucleotide probes prepared from the purified polypeptide to clone the genomic DNA fragment coding for the desired polypeptide. By means of different methods, such as primer extension, restriction, adapter insertion or ligation with linker oligonucleotides, a nucleotide insert containing the desired DNA sequence is constructed. Said sequence can then be mapped and sequenced by the known techniques.

Other techniques can also be envisaged, such as the use of DNA and/or partial or total chemical synthesis. These techniques are known and the structures described in FIGS. 9 and 14 enable those skilled in the art to isolate an equivalent sequence, in any microorganism, with the means known in the art.

The polypeptides whose structure is deduced from the above DNA sequences, and which possess an amidase activity, can be obtained from different microorganisms, and especially from *brevibacteria* or bacteria of the genus *Rhodococcus*. More precisely still, these polypeptides are prepared from cultures of natural or recombinant microorganisms by extraction and purification, the purification being carried out by a series of steps consisting in preparing a crude enzymic extract from the cell culture, fractionating this extract with ammonium sulfate and purifying it by various gel chromatography and filtration procedures. The details of these steps are given in the Examples.

The purified polypeptides can then be sequenced and their genes cloned and expressed in various recombinant microorganisms (host microorganisms) in accordance with common techniques of molecular biology (recombinant DNA technique). More precisely, the transformed microorganisms contain at least one cassette for expression of the DNA sequences as shown in FIGS. 9 and 14, these cassettes preferably consisting of one of said DNA sequences under the dependence of DNA sequences ensuring its expression in the host in question. Said cassette can be a cassette integrated directly into the genome of the host, or a cassette inserted into a plasmid which also contains an origin of plasmid replication active in the host and a selection means.

The DNA sequences ensuring the expression of the afore-mentioned DNA sequences preferably contain a transcription and translation initiation region.

In this process, the transcription and translation initiation regions contain a promoter and a ribosome binding site. These regions can be homologous or heterologous with the polypeptide produced.

The choice of these regions depends especially on the host used. In particular, in the case of procaryotic host microorganisms, the heterologous promoter can be selected from strong bacterial promoters such as tryptophan operon promoter Ptrp, lactose operon promoter Plac, phage lambda right promoter $P_R$, phage lambda left promoter $P_L$, the strong promoters of *corynebacteria* phages or else the homologous promoters of *corynebacteria*. More particularly, in the case of phage lambda right promoter, the thermosensitive form $P_RcI^{Ts}$ may be preferred. In the case of eucaryotic microorganisms such as yeasts, the promoters can be derived from glycolytic yeast genes such as the genes coding for phosphoglycerate kinase (PGK), glyceraldehyde 3-phosphate dehydrogenase (GPD), lactase (LAC4) and enolase (ENO).

As regards the ribosome binding sites, that derived from the lambda cII gene and those derived from homologous genes of *corynebacteria* are used preferentially when the host microorganism is procaryotic.

A region permitting termination of the translation and functional transcription in the envisaged host can be positioned at the 3' end of the coding sequence. The plasmid also comprises one or more markers for selecting the recombinant host. The preferred markers are dominant markers, i.e. those which impart resistance to antibiotics such as ampicillin or streptomycin, or to other toxic products.

Among the host microorganisms used, there may be mentioned especially enterobacteria such as *E. coli*, and *corynebacteria* such as those belonging to the genera *Corynebacterium, Brevibacterium* or *Rhodococcus*.

Of course, other cell types can be used according to the same principle.

According to the invention, ammonium adipate is prepared simply by bringing adipamide and/or ammonium adipamate (reactants) into contact with a polypeptide or a recombinant microorganism as described above. The reaction is generally carried out at room temperature.

In one particular embodiment of the invention, the polypeptide or the recombinant microorganism containing the polypeptide is immobilized on or in a solid support.

The Examples which follow provide an illustration of the characteristics and advantages of the present invention, without however limiting its scope.

DESCRIPTION OF THE FIGURES

FIG. 1: Table describing the different steps of the purification of the enantioselective amidase of *Brevibacterium* R 312.

a—from 40 g of wet cells, after precipitation with streptomycin sulfate.

b—one unit (U) is equivalent to 1 μmol of HPPAcid formed per hour under the conditions described below.

FIG. 2:

a—peptide sequences (N-terminal (SEQ ID NO:1) and internal (SEQ ID NO:2) obtained from the purified solution of *Brevibacterium* R 312.

b—oligonucleotide probe (SEQ ID NO:3) produced from the internal fragment (SEQ ID NO:4).

a—strategy for the preparation of the probe sq 918 from the N-terminal fragment.

FIG. 3b—probe (SEQ ID NO:9) sq 918 obtained.

Figure 4A:
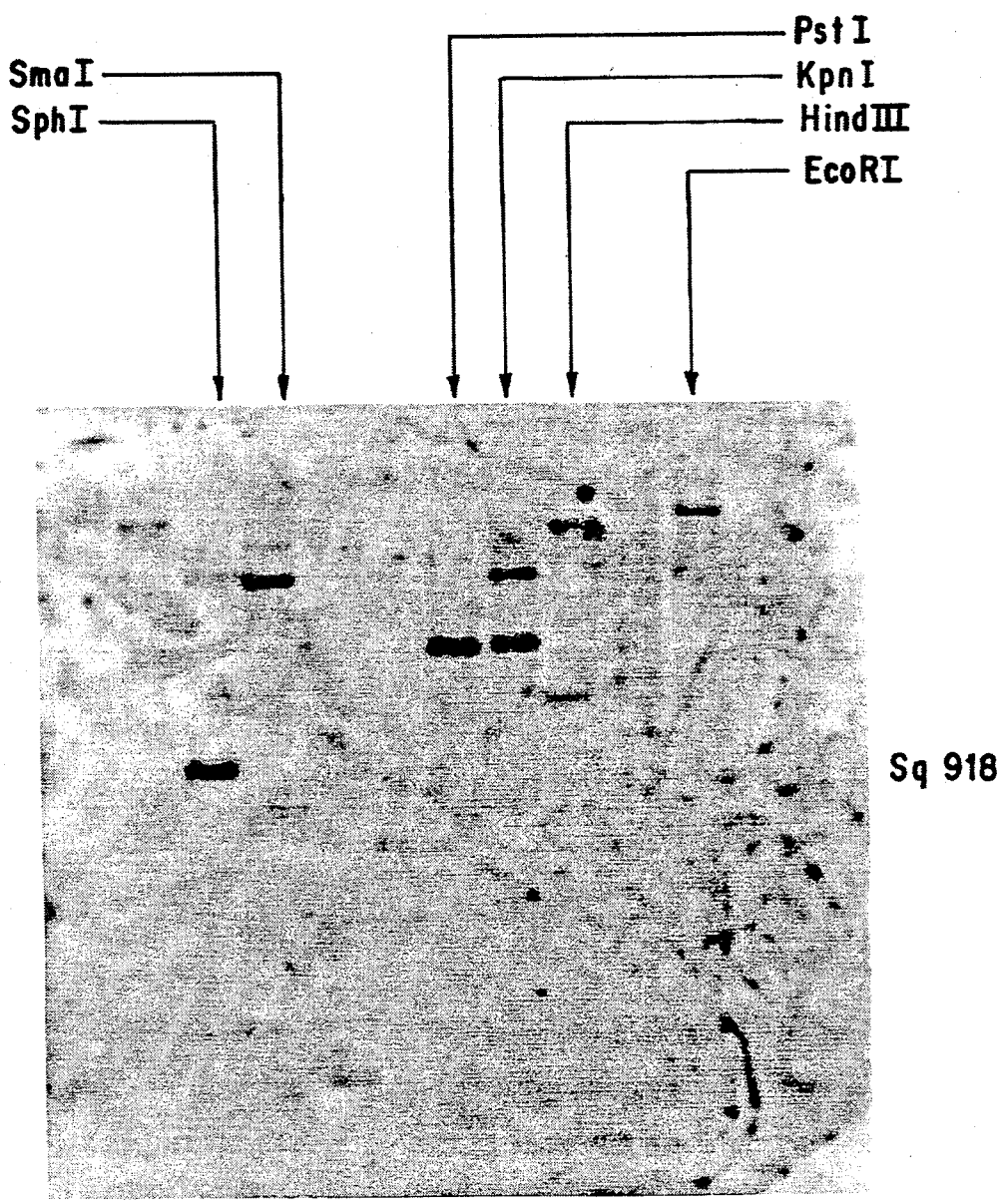

FIG. 4a—hybridization profile of the probe sq 918 with the total genomic DNA of *Brevibacterium* R 312 digested with the enzymes *EcoRI, HindIII, KonI, PstI* and *SohI*.

Figure 4B:
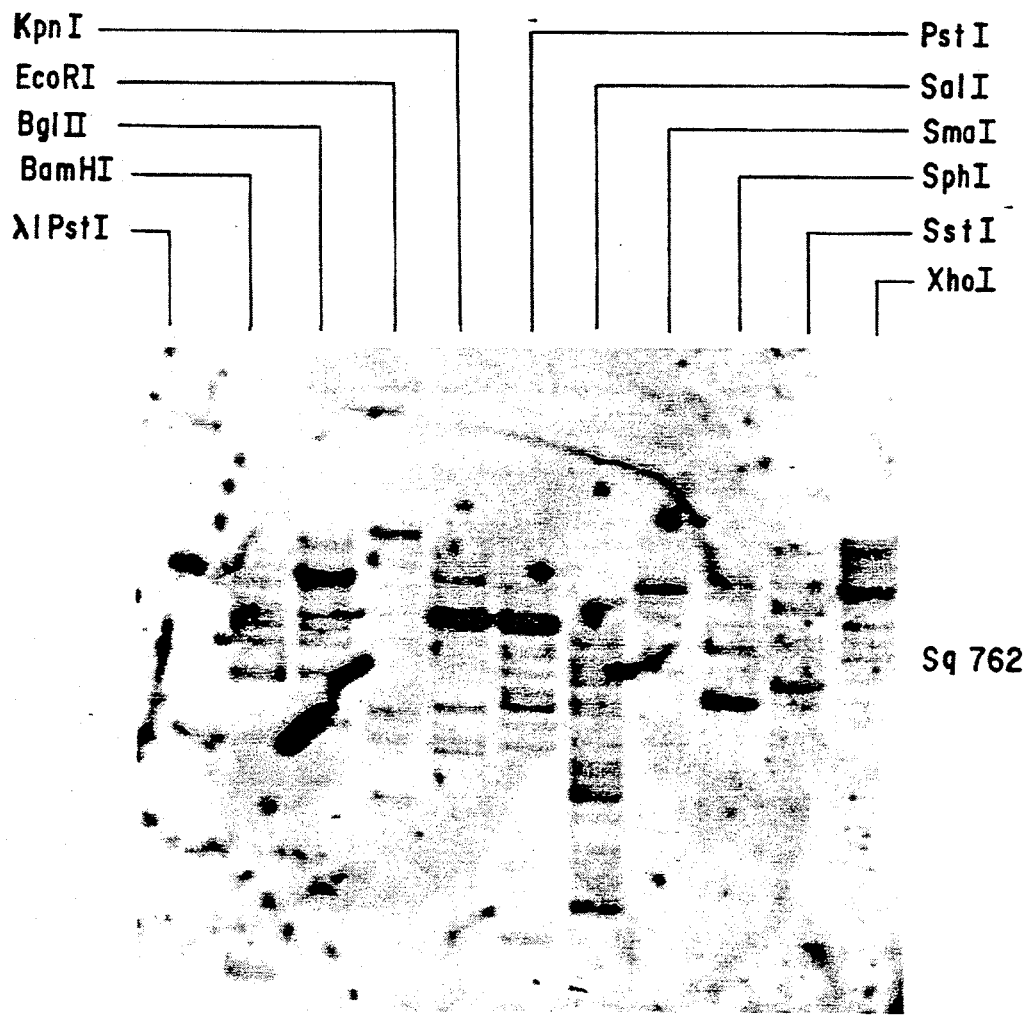

FIG. 4b—hybridization profile of the probe sq 762 with the total genomic DNA of *Brevibacterium* R 312 digested with the same enzmes as (a).

Figure 5:
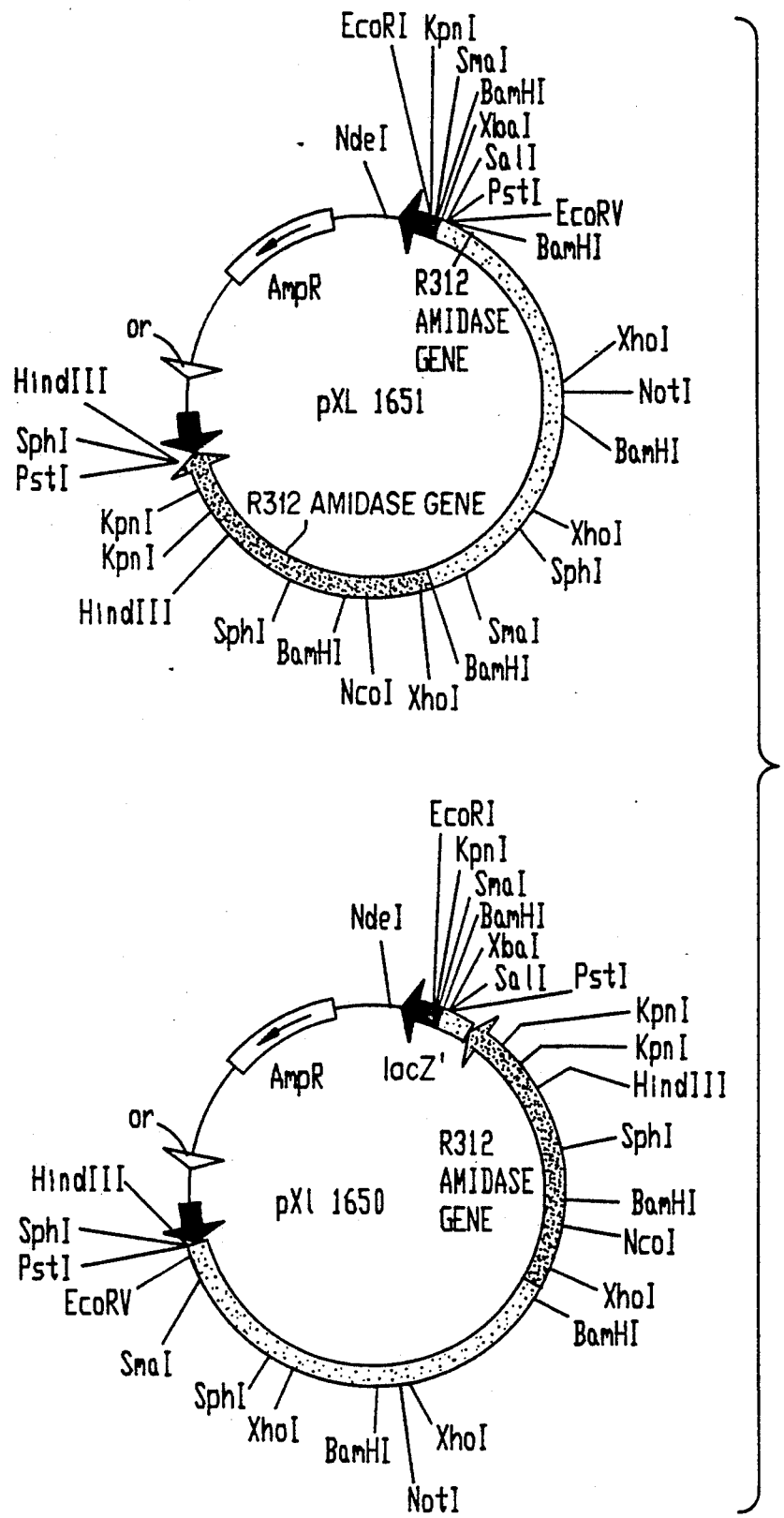

FIG. 5: Restriction maps of plasmids pXL1650 and pXL1651.

Figure 6:
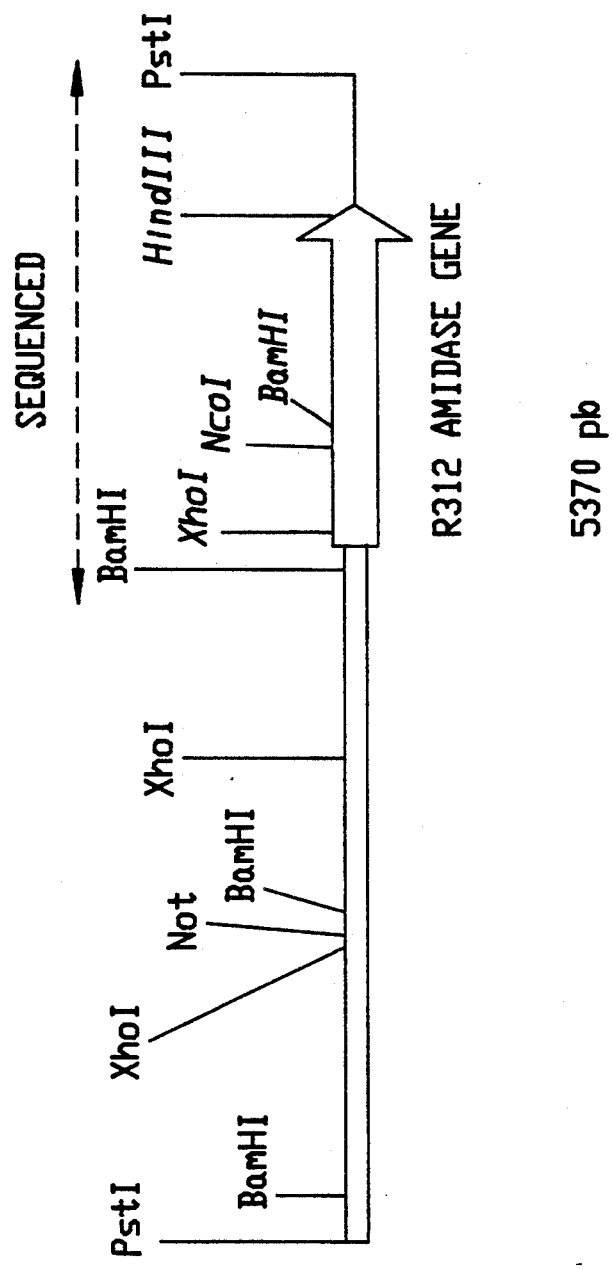

FIG. 6: Restriction map of the PstI fragment of 5.4 kb containing the gene of the enantioselective amidase of *Brevibacterium* R 312.

Figure 7:
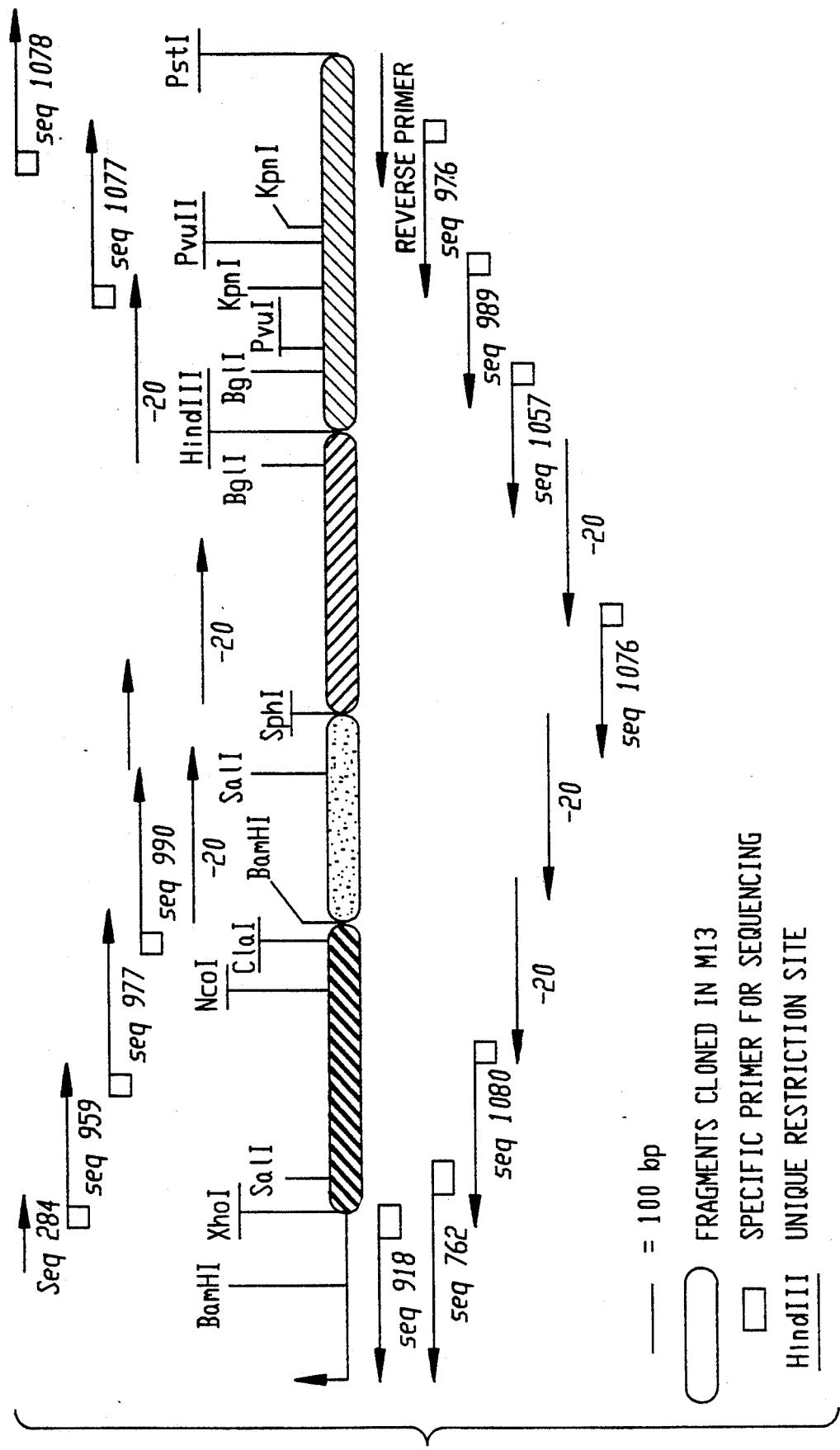

FIG. 7: Sequencing strategy for the *BamHI-PstI* fragment containing the gene of the enantioselective amidase of *Brevibacterium* R 312.

Figure 8:
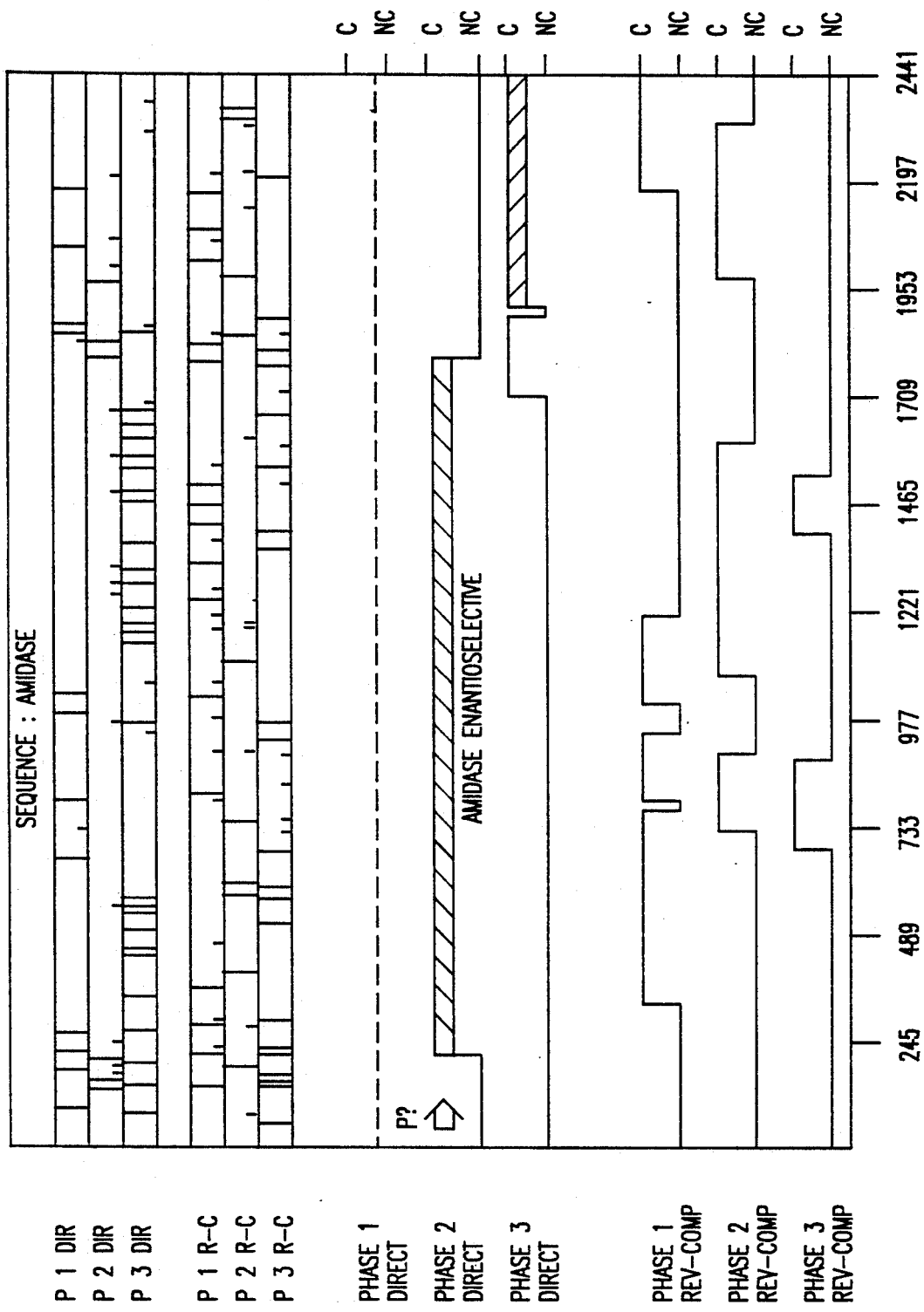

FIG. 8: Analysis of the open reading frames of the sequenced fragment.

FIG. 9A-9C Nucleotide (SEQ ID NO:10) and peptide (SEQ ID NO:11) sequences of the enantioselective amidase of *Brevibacterium* R 312.

Figure 10:
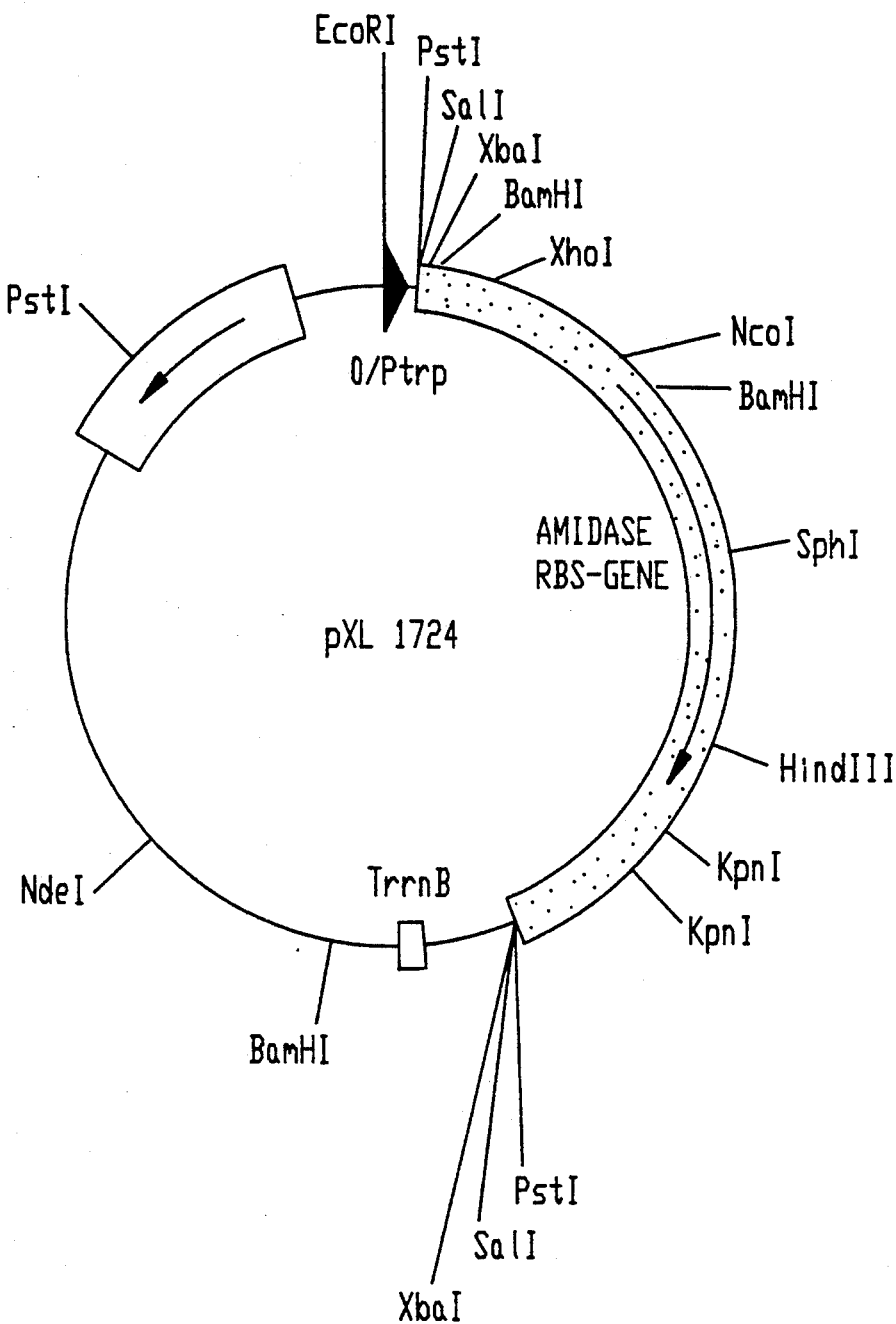

FIG. 10: Restriction map of plasmid pXL1724.

Figure 11:
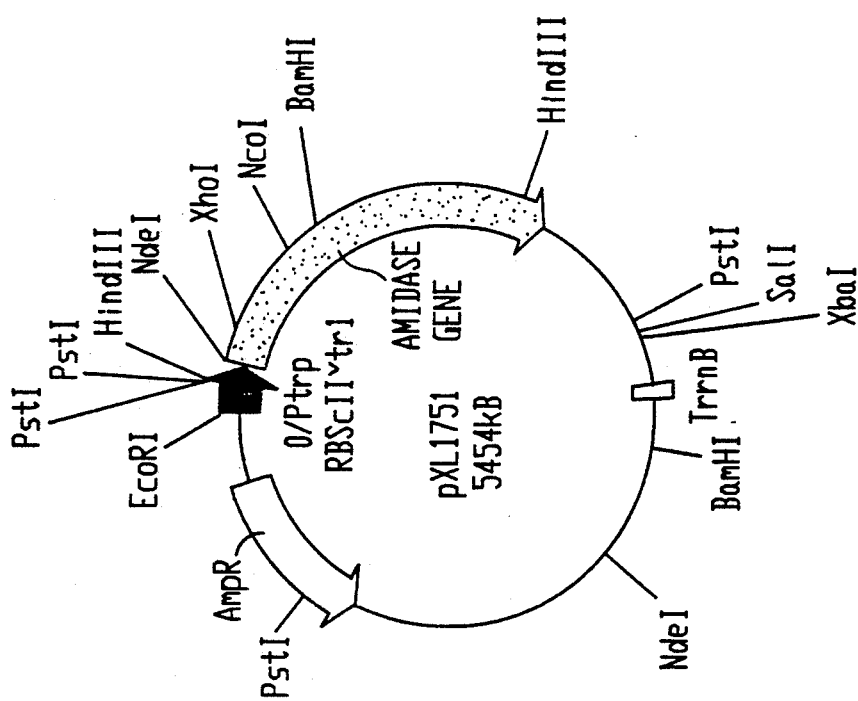

FIG. 11: Restriction map of plasmid pXL1751.

Figure 12:
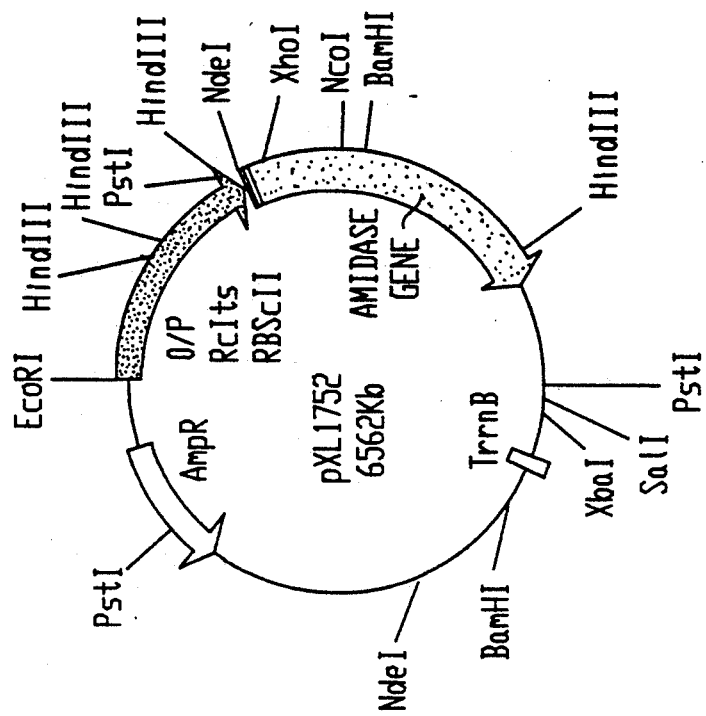

FIG. 12: Restriction map of plasmid pXL1752.

Figure 13:
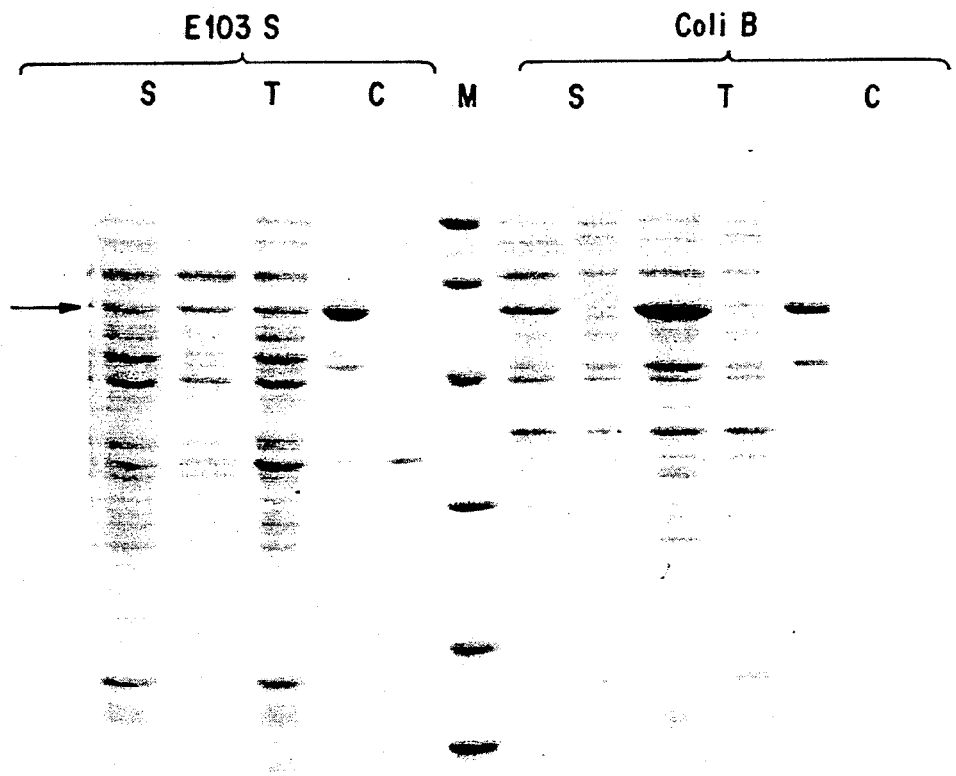

FIG. 13: Polyacrylamide-SDS gel at 12.5% after staining with Coomassie blue, demonstrating the expression of the enantioselective amidase of *Brevibacterium* R 312 from the strains coli B and E103S. Each lane corresponds to an amount of protein equivalent to 60 μl of the culture at an optical density of 2.1 (E103S) and 0.7 (coli B) at 610 nm. T), sonicated fraction; S), soluble fraction; C), insoluble fraction. The reference plasmids (pXL1029 and pXL906) contain the IL1beta gene under the control of promoters $P_RcI^{ts}$ and Ptrp respectively.

FIG. 14A-14C: Nucleotide (SEQ ID NO:12) and peptide (SEQ NO NO:13) sequences of the enantioselective amidase of a rhodococcus.

FIG. 15: Nucleotide (SEQ ID NO:14) and peptide (SEQ ID NO:15) sequences of the 150-200 region.

FIGS. 16 and 17: Sequence homology studies: search for the active site.

Figure 18:
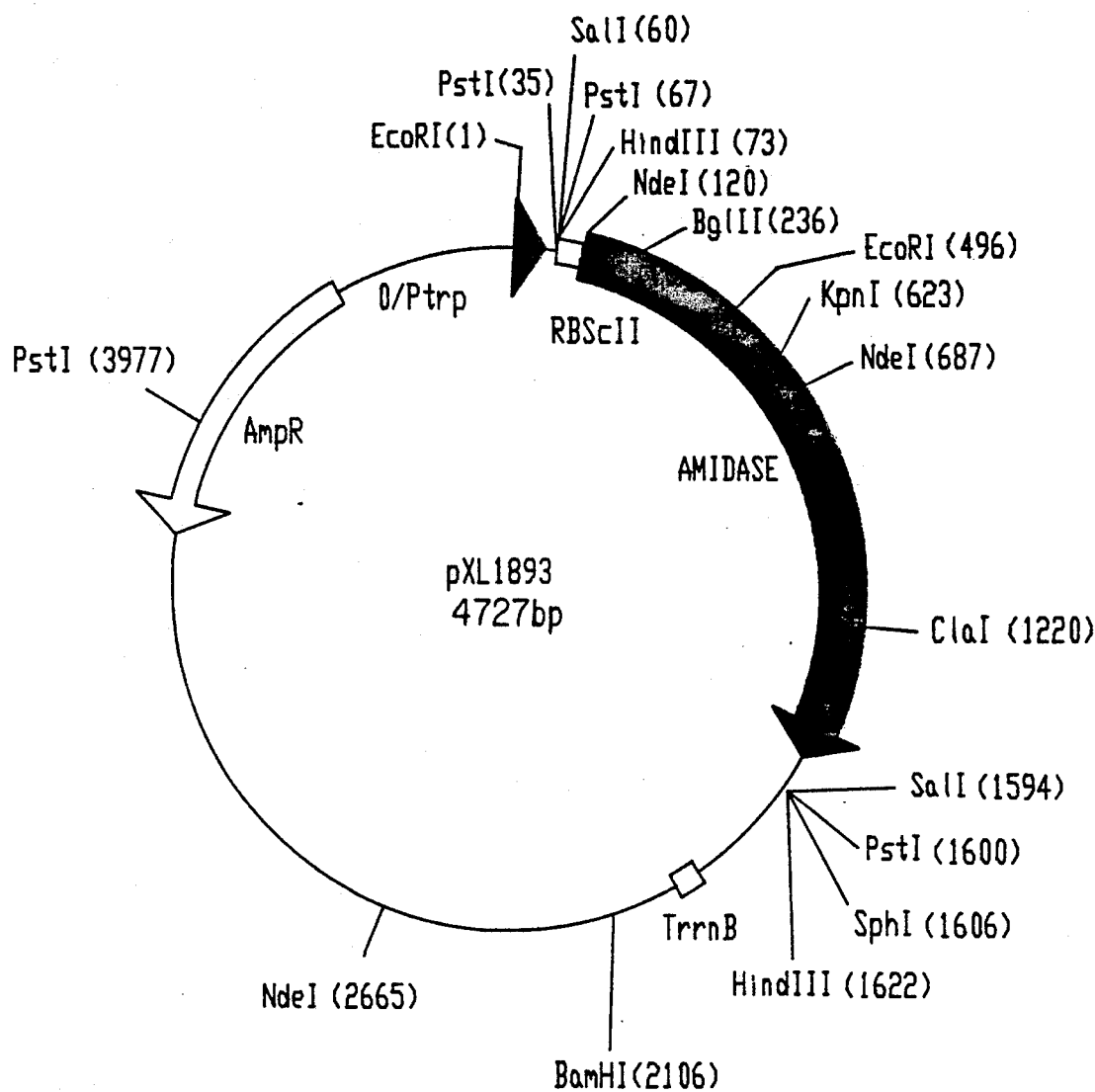

FIG. 18: Vectors for expression in *E. coli* of the Amd sequences shown in FIGS. 14 and 15.

Figure 19:
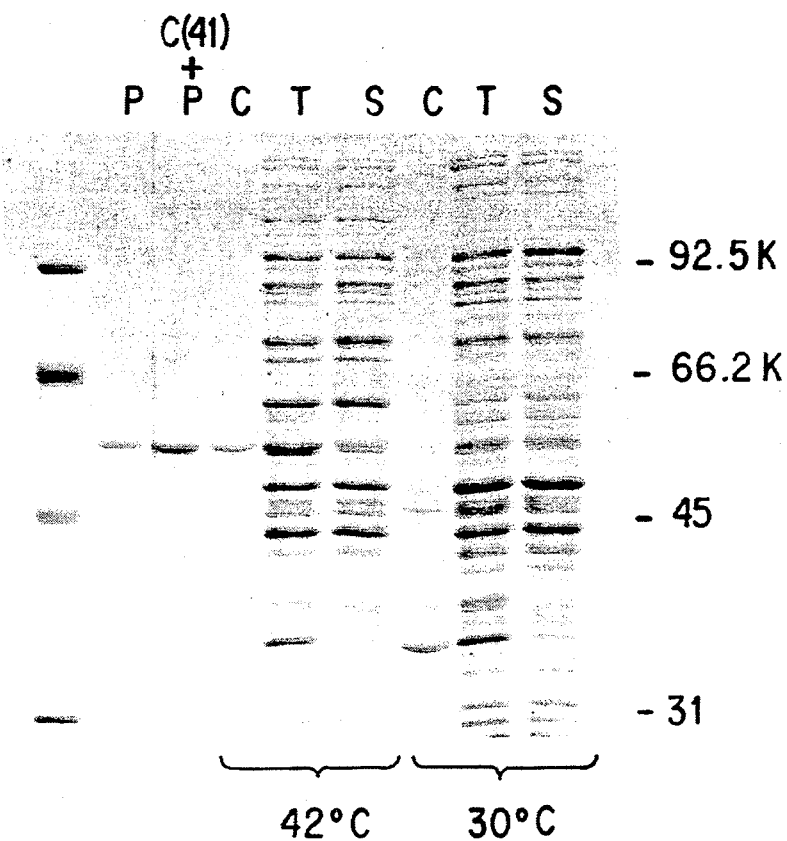

FIG. 19: Result of expression with the E. coli strain E103S transformed by plasmid pXL1894.

Figure 20A:
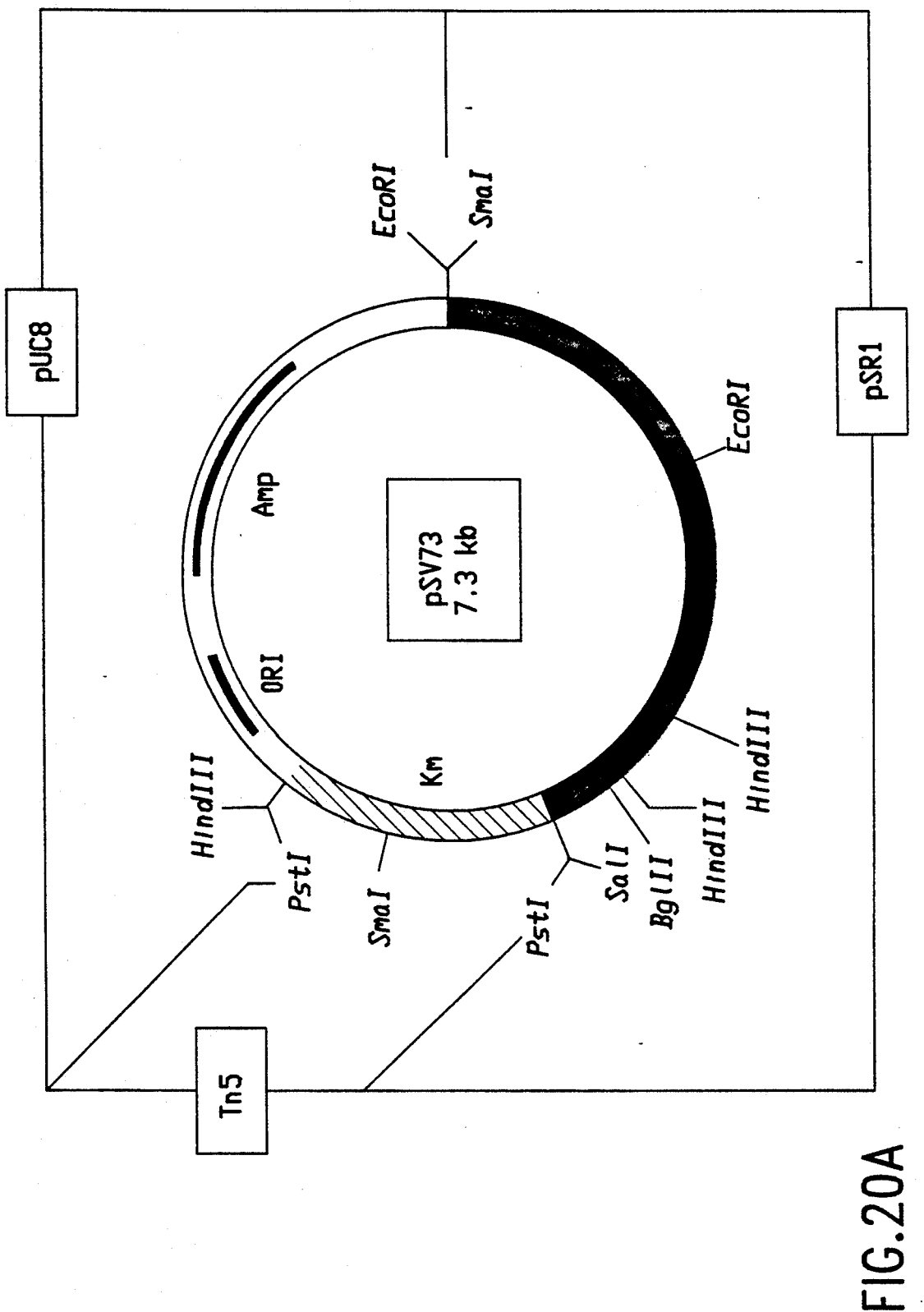
Figure 20B:
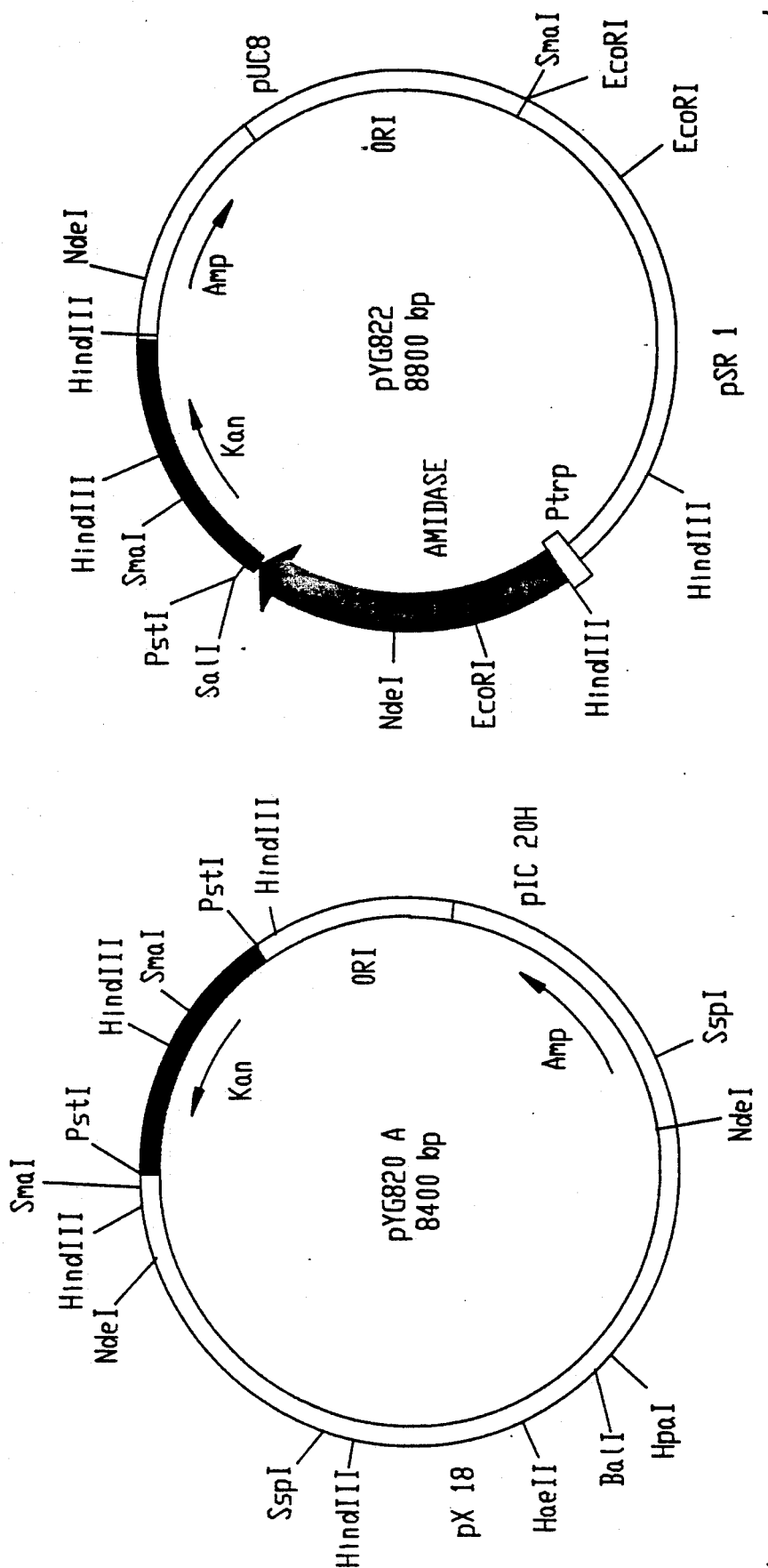

FIGS. 20A-20B: Vectors for expression in corynebacteria of the Amd sequences shown in FIGS. 14 and 15.

STARTING PLASMIDS

Plasmid pXL534 is derived from pXL276 (which contains Ptrp-RBScIIΔtRI-HSA: European patent 86 400617.6) by deletion of a fragment of 2.1 kb with the enzyme Ba131 from the EcoRV site, and ligation to a BamHI linker.

Plasmid pXL820 is derived from plasmid pXL534 by excision of the *EcoRI-NdeI* fragment carrying Ptrp and RBScIIΔtRI, and insertion of an *EcoRI-NdeI* fragment containing promoter $P_R cI^{ts}$ and the RBScIIΔtRI site. The latter is derived from plasmid pRK248cI$^{Ts}$ (Bernard et al., Gene, 5, 59-76) by means of the following steps:

- excision of a *BoII-BcII* fragment from pRK248cI$^{ts}$ containing $P_R cI^{ts}$.
- insertion of this fragment at the BamHI site of plasmid pUC19.
- linearization of the resulting pUC19 with ClaI and filling of the ends with Klenow DNA polymerase.
- additional digestion with *SmaI* and ligation.
- *EcoRI-SalI* fragment containing $P_R cI^{ts}$ is excised from this new construction and inserted into pXL534 opened with these two enzymes.
- the *EcoRI-NdeI* fragment is then excised from this plasmid and contains $P_R cI^{ts}$-RBScIIΔtRI.

EXAMPLE 1

Identification and Purification of the Enantioselective Amidase of *Brevibacterium* R 312

1.1. - Identification

R,S-2-(4-Hydroxyphenoxy)propionamide, a 2-aryloxypropionamide derivative, is a better substrate for the enantioselective amidase than the 2-arylpropionamide derivatives, especially 2-phenylpropionamide and 2-(3-benzoylphenyl)propionamide. Furthermore, the selectivity of the amidase towards the R enantiomer of HPPAmide is representative of the selectivity towards the S enantiomer of the 2-arylpropionamide derivatives.

Consequently, the enantioselective enzymic activity was detected by using 2-(4-hydroxyphenoxy)propionamide (HPPAmide) as the substrate. The reaction is carried out at 25° C., with shaking, in a 50 mM sodium phosphate buffer, pH 7.0, in the presence of *Brevibacterium* R 312, and is stopped by the addition of a 55/40/5 (v/v) mixture of 0.05 M phosphoric acid, acetonitrile and 1 N HCl. The culture is then centrifuged and the supernatant is analyzed by reversed-phase HPLC (Hibar-Merck RP-18; 5 μm). Elution is effected with an 85/15 (v/v) solution of 0.005 M phosphoric acid and acetonitrile and the respective concentrations of HPPAmide and HPPAcid are measured by the position of the elution peaks and compared with a standard. The enantiomeric excess, defined as the ratio $(R-S)/(R+S)$ x 100, in which R and S are the respective concentrations of the R and S enantiomers of the HPPAcid, is deduced either from polarimetric measurements (using the sodium absorption at 589 nm) or from HPLC analysis on a chiral column.

The activities obtained with whole cells and a soluble extract are respectively 15 U/mg and 24 U/mg of protein (1 U=1 μmol of HPPAcid formed per hour). The enantiomeric excess of the R HPPAcid formed is 95%. These results show that *Brevibacterium* R 312 possesses an enantioselective amidase activity which is capable of hydrolyzing racemic 2-arylpropionamides to the corresponding S acids. This was verified with hydrolyses of racemic 2-phenylpropionamide and racemic 2-(3-benzoylphenyl)propionamide, which respectively give the corresponding S acids with enantiomeric excesses of more than 93%.

1.2. Purification

The purification is carried out at 4° C.

The cells (40 g by dry weight of *Brevibacterium* R 312) are thawed and taken up in 300 ml of buffer A (50 mM sodium phosphate, pH 7, 5 mM β-mercaptoethanol). The cells are then broken by ultrasound and the membrane debris is removed by centrifugation at 20,000 g for 30 minutes. 25 ml of a 10% solution of streptomycin sulfate are added slowly to 30 ml of supernatant, with shaking. After 45 minutes, the solution is clarified as above and the supernatant is treated with ammonium sulfate. The protein fraction precipitating between 30.8% and 56.6% of ammonium sulfate saturation is recovered by centrifugation and dissolved in 35 ml of buffer A before being dialyzed for a longer period against this same buffer. The resulting solution is then adjusted to 20% of ammonium sulfate saturation, centrifuged again and applied to a phenyl-Sepharose CL-4B column (Pharmacia) equilibrated with buffer A at 20% of ammonium sulfate saturation. The protein fractions containing the enzymic activity are then eluted with the same buffer and concentrated by ultrafiltration with an AMICON DIAFLO PM 10 cell to a volume of 18 ml. 10% glycerol is then added to the concentrated fraction and the solution obtained is loaded on to an Ultrogel AcA 44 column (IBF-biotechnics France) equilibrated beforehand with 50 mM Tris-HCl, pH 7.0, 100 mM NaCl. The protein fractions containing the greatest specific activity (about 32% of the total activity loaded on to the column) are collected, concentrated and subjected to an additional filtration step on the same gel. Likewise, the fractions having the greatest specific activity (about 30% of the proteins applied to the column) were analyzed by SDS-PAGE and stored. The enantioselectivity of the protein purified in this way was also determined.

These purification steps made it possible to obtain an enzyme with a purity of more than 80% and a specific activity of 815 U/mg. At this stage, a majority band with an apparent molecular weight of 59±5 KD, corresponding to at least 80% of the total proteins, is visible in SDS-PAGE. Furthermore, the amidase activity eluted from the Ultrogel AcA 44 also corresponds to a molecular weight of 63±5 KD, indicating that the enzyme is apparently in monomeric form.

EXAMPLE 2

Cloning of the Enantioselective Amidase of *Brevibacterium* R 312

2.1. Determination of protein sequences

The peptide sequences corresponding respectively to the N-terminal end (27 residues) and to an internal tryptic fragment (21 residues) of the enantioselective amidase of *Brevibacterium* R 312 were determined on the enzyme purified in this way.

To do this, 3 nmol of the amidase preparation were reduced and carboxymethylated. The majority protein compound is then desalted and purified to homogeneity by reversed-phase HPLC. The N-terminal sequence is then determined by Edman's automatic sequential degradation method using an "Applied Biosystems Model 470A" apparatus. The sequence shown in FIG. 2a is obtained by this procedure. To determine an additional internal sequence, the same amount of protein is subjected to a tryptic digestion. The reduced and carboxymethylated fragments are then separated off by reversed-phase HPLC (2.1×10 mm; flow rate: 0.2 ml/min) using the following elution buffer: gradient of to 50% of acetonitrile in 0.07% trifluoroacetic acid. A peptide eluted in a well-separated peak (at 40.8% of acetonitrile) is sequenced (FIG. 2a).

2.2. Preparation of the nucleotide probes

Two types of strategy were pursued for the construction of the nucleotide probes.

In the first strategy, a 29-mer probe (minimum homology of 59%) was constructed, allowing for the use of the codons in the tryptophan operon of *Brevibacterium lactofermentum* (sequence of 7.7 kb containing 6 cistrons: Matsui et al., Mol. Gen. Genet., 209, p. 299, 1987) and according to the sequence IDGALGSYDV (SEQ ID NO:4) of the internal fragment (having a lower average degeneracy). The non-coding strand was synthesized by considering the relative thermodynamic neutrality of G=T pairings and by introducing a few degeneracies in order to maximize the average theoretical frequency of the codons in question (88% relative to the use of the chosen codons). The result of the considerations is to bring the GC content of the probe to about 69%. The probe obtained (sq 762) is given in FIG. 2b.

In a second type of strategy, the PCR method described by Girgés et al. (Nucleic Acids Res., 16, p. 10371, 1988) was used to give an exact nucleotide probe from a peptide corresponding to highly degenerate codons. To do this, synthetic 25-mer oligonucleotides (see underlined sequence in FIG. 3), corresponding to all the possible ways of cloning the first five or last five codons of the N-terminal peptide sequence and containing restriction sites at their 5' ends (respectively *EcoRI* and *HindIII*), were used to prime an enzymic amplification of the genomic DNA of *Brevibacterium* R 312. After 30 amplification cycles, the candidate fragment is purified on gel and then inserted between the *HindIII* and *EcoRI* sites of bacteriophage M13mp19. A number of clones, obtained after cloning of the resulting fragment at two different primer hybridization temperatures (45° C. and 48° C.), were then sequenced and compared. The results are indicated in FIG. 3. This Figure shows that, apart from the degeneracies introduced by the primers, a DNA fragment (unique between the primers) coding for the N-terminal end of the amidase has indeed been amplified. A synthetic 40-mer oligonucleotide corresponding to this internal fragment was therefore used for the remainder of the cloning as an exact probe of the N-terminal end of the amidase. The sequence of this fragment sq 918 is indicated in FIG. 3.

The two probes obtained in this way were labeled with $^{32}$p by the 5' phosphorylation method.

2.3. Cloning of the gene of the enantioselective amidase of Brevibacterium R 312

The strategy followed consisted initially in verifying the specificity of the synthesized probes and determining by Southern blotting the nature of the genomic DNA fragment to be cloned. Briefly, genomic DNA of *Brevibacterium* R 312 was digested alternately with several restriction enzymes corresponding to sites usable for cloning, and especially to sites present in the multiple cloning site of plasmids of the pUC series. The enzyme PstI was used in particular. After electrophoresis on agarose gel and transfer on to a nylon membrane, the various digestions were hybridized with the probes sq 762 and sq 918. The results given in FIG. 4 show that the two probes are characterized by a sufficient specificity under hybridization con-ditions (at most one fragment hybridizing for each digestion). Furthermore, insofar as the two probes make it possible to obtain approximately the same hybridization profile, it may be considered that the hybridization signals are very specific for the desired gene and that the internal peptide obtained after tryptic hydrolysis is very close to the N-terminal end. The hybridization blots show in particular the existence of a unique PstI fragment of about 5.4 kbp which hybridizes very strongly with the two probes. It was therefore decided to clone this fragment. To do this, all the fragments with a size of between about 4.6 to 5 kbp and about 6 to 6.5 kbp, resulting from a total genomic digestion of *Brevibacterium* R 312 with *PstI*, were purified on agarose, electroeluted and then ligated to vector pUC19 digested with PstI beforehand. After transformation in the *E. coli* strain DH5α, 500 white colonies, corresponding theoretically to recombinant microorganisms, were obtained on X-gal medium. These colonies were subcultured individually, transferred on to a nylon membrane and then analyzed by hybridization with the $^{32}$p-labeled probe sp 918. Two clones were thus identified as hybridizing very strongly with the probe, and were isolated and retained for continuing the cloning.

The two recombinant plasmids pXL1650 and pXL1651 isolated from these two clones were analyzed by various methods, namely restriction mapping, partial sequencing using the probes as sequencing primers, and Southern blotting. The results given in FIG. 5 show that the two plasmids contain the same PstI insert of about 5.4 kbp in both orientations. FIG. 6 shows a restriction map of this fragment. These two plasmids do indeed contain the sequences coding for the characterized peptides, the tryptic fragment being next to the N-terminal end (FIG. 9). Furthermore, these results show that the gene coding for the enantioselective amidase of *Brevibacterium* R 312 is located on a BamHI-PstI fragment of about 2.4 kbp and oriented in the BamHI to PstI direction. Given the position of the 5' end of the coding sequence and in the knowledge that the enzyme is coded for by at most 2 kbp (monomer of 57–63 KD, depending on the estimation), it was therefore certain that the complete gene was contained in the BamHI-PstI fragment, so sequencing of the latter was undertaken.

EXAMPLE 3

Sequence of the *BamHi-PstI* Fragment Containing the Gene of the Enantioselective Amidase of *Brevibacterium* R 312

The sequencing strategy for the *BamHi-PstI* fragment is indicated in FIG. 7. The various sequences were all obtained by the chain termination method (sequenase kit in the presence of 7-deaza dGTP; (S$^{35}$)dATP), either on single-stranded templates of recombinant M13 carrying subfragments, or directly on plasmid pXL1650. Several specific primers were also synthesized for this purpose. The average GC content of the sequence obtained is 61.5%. An analysis of the open reading frames obtained is given in FIG. 8. This figure shows that the open reading frame corresponding to the N-terminal end of the amidase codes for 521 amino acids corresponding to a molecular weight of 54,671. It is seen on this open reading frame that the GC content is respectively 65.8, 52.5 and 70% for the first, second and third codon positions, which is a characteristic distribution in the coding sequences of microorganisms rich in GC. The complete sequence of the BamHi-PstI fragment is given in FIG. 9.

EXAMPLE 4

Expression of the Gene of the Enantioselective Amidase of *Brevibacterium* R 312 in *E. coli*

4.1. Construction of the plasmids

Several constructions were prepared in which the structural gene of the amidase, containing a ribosome binding site homologous with or derived from the phage lambda cII gene, is placed under the control of its own promoter, tryptophan operon promoter or thermosensitive phage lambda right promoter. Plasmid pXL1650 (FIG. 5) was obtained by insertion, into the unique PstI site of plasmid pUC19, of the fragment of 5.4 kbp resulting from the digestion of the total genomic DNA of *Brevibacterium* R 312 with PstI. This plasmid therefore contains lactose operon promoter Plac, followed by the ribosome binding site and the structural gene of the enantioselective amidase of *Brevibacterium* R 312, as well as an ampicillin resistance gene.

Plasmid pXL1724 (FIG. 10) was obtained by insertion, into a vector containing tryptophan operon promoter, of the *BamHi-PstI* fragment of 2.26 kbp excised by treatment of the fragment of 5.4 kbp with the enzyme *BamHI*. This fragment contains the complete gene of the enantioselective amidase of *Brevibacterium* R 312, preceded by the 58 base pairs upstream from the ATG codon carrying the ribosome binding site.

Two other constructions were prepared in which the structural gene of the enantioselective amidase of *Brevibacterium* R 312 is placed under the control of heterologous promoters and heterologous ribosome binding sites. These plasmids (pXL1751 and pXL1752) were obtained in the following manner:

Plasmid pXL1724 was mutagenized by the PCR method so as to introduce an NdeI cleavage site, CATATG, in place of the ATG codon situated upstream from the structural gene of the amidase. The amplification was performed using a primer corresponding to the NdeI cleavage site hybridizing with the ATG start codon, and a primer corresponding to the XhoI cleavage site situated a few base pairs downstream from the ATG codon. The amplified fragment was then excised by cleavage with the two enzymes *NdeI* and *XhoI*.

Use of promoter Ptrp:

An *EcoRI-NdeI* fragment containing promoter Ptrp and the ribosome binding site of the lambda cII gene, not containing the terminator sequence $tR_1$ and the 5' region of the structural gene of the amidase, was inserted into plasmid pXL1724 opened with *EcoRI* and *XhoI*, in order to generate plasmid pXL1751 (FIG. 11).

Use of promoter $P_RcI^{ts}$:

The same strategy was employed, this time using the *EcoRI-NdeI* fragment of plasmid pXL820 containing promoter $P_RcI^{ts}$ and the ribosome binding site of the lambda cII gene, not containing the sequence $tR_1$. This gave plasmid pXL1752 (FIG. 12).

4.2. Expression of the amidase of Brevibacterium R 312 in coli B and E103S

Plasmids pXL1751 and pXL1752 were used to transform the strains coli B and E103S, respectively, by the calcium chloride method. The recombinant microorganisms are selected on ampicillin medium.

The expression of the enantioselective amidase of *Brevibacterium* R 312 was measured, after sonication of the cells, by SDS-PAGE in the crude fraction or, after centrifugation, in the residue and in the supernatant. The results are given in FIG. 13 and show a high level of expression of the amidase, which represents up to 20% of the total proteins.

EXAMPLE 5

Purification of the Enantioselective Amidase of a Rhodococcus

I. Assay of the enzymic activity

The fraction containing the activity is incubated for 30 min at 30° C. in 500 μl of 0.1 M Tris/HCl buffer, pH 7.5, containing 5 mM DTT and 18.1 mM 2-phenylpropionamide. After incubation, 2 ml of an acetonitrile/1 N HCl mixture (90/10) and then 2 ml of a 50 mM $H_3PO_4/CH_3CN$ mixture (75/25) are added to the incubation mixture. After centrifugation at 5000 g for 10 min, an aliquot of the supernatant is injected into an HPLC apparatus for assay of the reaction products.

Column: Nucleosil 5-C18 25 cm
Eluent: 50 mM $H_3PO_4/CH_3CN$ (75/25)
Injection: 10 μl
Flow rate: 1 ml/min One activity unit is defined as the amount of enzyme required to hydrolyze 1 μmol of 2-phenylpropionamide per h.

II. Purification protocol

1. Preparation of the enzymic extract 7 g of cells are suspended in 15 ml of 0.1 M Tris/HCl buffer, pH 7.5, 5 mM DTT and broken by sonication for 15 min at 4° C. The crude enzymic extract is recovered by centrifugatron for 1 h at 50,000 g.

2. First ion exchange chromatography 20 ml of buffer A—25 mM Tris/HCl, pH 7.5, 5 mM DTT—are added to this crude extract (20 ml). The sample is injected at a rate of 3 ml/min on to a Mono Q HR 10/10 column (Pharmacia) equilibrated in buffer A. After the column has been washed, the proteins are eluted with a linear KCl gradient (0 to 1 M) developed over 1 h at 3 ml/min. 6 ml fractions are collected. The amidase is eluted over 18 ml with about 0.3 M KCl.

3. Second ion exchange chromatography

The fractions containing the activity are pooled and concentrated to 2 ml using a Centriprep ultrafiltration module (Amicon). After dilution with 6 ml of buffer A, 4 ml of this sample are injected at 1 ml/min on to a Mono Q HR 5/5 column equilibrated in buffer A. The proteins are eluted with a linear KCl gradient (0 to 0 5 M) in buffer A. The fractions are pooled and the sample is brought to a glycerol concentration of 15% (vol/vol) and finally concentrated to 1 ml as above.

4. Hydrophobic chromatography 1 ml of the buffer 0.1 M Tris/HCl, pH 7.5, 0.5 mM DTT, 1.7 M $(NH_4)_2SO_4$ (buffer B) is added to the sample, which is then injected (in two portions) on to a phenyl-Superose HR 5/5 column (Pharmacia) at a rate of 0.25 ml/min. The proteins are eluted at 0.5 ml/min with an increasing linear $(NH_4)_2SO_4$ gradient (1.7 M to 0 M) over 25 ml. 0.5 ml fractions are collected. The active fraction is brought to a glycerol concentration of 15% and then diluted with 1 ml of buffer A.

5. Chromatography on hydroxyapatite

The sample is injected at 0.5 ml/min on to a Bio-Gel HPHT column (Bio-Rad) equilibrated in the buffer 85 mM Tris/HCl, pH 7.5, 0.5 mM DTT, 10 μM CaCl$_2$, 15% glycerol (buffer C). The amidase is eluted at a rate of 0.5 ml/min with a linear gradient of 0 to 100% of the buffer 0.35 M potassium phosphate, pH 7.5, 0.5 mM DTT, 10 μM CaCl$_2$, 15% glycerol, in buffer C over 20 min.

These various steps make it possible to obtain an enzyme purified to homogeneity with a specific activity of 988 U/mg of protein.

Like that of Brevibacterium R 312, the resulting enzyme behaves like a dimer of identical subunits with an apparent molecular weight of 53 KD±2 KD.

EXAMPLE 6

Cloning of the Gene of the Amidase Obtained in Example 5

After a further purification step on TSK-G3000 SW, the enzyme was subjected to a sequencing operation. As the N-terminal end was inaccessible to Edman's chemistry, a total hydrolysis with trypsin was carried out and three HPLC fractions of the hydrolyzate—123, 124 and 162—gave peptides making it possible to obtain an unambiguous sequence. The following three 32-mer nucleotide probes, corresponding to mixtures of 8 to 16 oligonucleotides and each containing 7 inosines in at least triply degenerate positions, were synthesized on the basis of these data:

PROBE A (peptide 123) (SEQ ID NO: 16; SEQ ID NO: 17)
```
     A T V D V  P V P D Y A
5'                                3'
     GCIACIGTIGATGTICCIGTICCIGATTATGC
            C          C C
```

PROBE B (peptide 124) (SEQ ID NO: 18 ; SEQ ID NO: 19)
```
     E A  G E L V P A T D Y
5'                                3'
     GAAGCIGGIGAACTIGTICCIGCIACIGATTA
          G     GT       C
```

PROBE C (peptide 162) (SEQ ID NO: 20)
5'                                3'
```
     CAAGATATIGATGTICTIATIGCICCIACIGT
            G  C    C T
```

The efficacy of these probes, $^{32}$P-labeled at the 5' end, was then tested by Southern transfer on to genomic DNA of Rhodococcus digested beforehand with one of the following restriction enzymes: SstI, SphI, SmaI, PstI. KpnI, EcoRI, SalI and BamHI. The experimental conditions were as follows: hybridization buffer: 5×SSC, 5×Denhardt, 0.1% SDS, 50 mM Na$_3$PO$_4$, pH 6.5, 250 g/ml ssDNA; hybridization temperatures: 50° or 55° C. (2 experiments); washing conditions: 1 h, 6×SSC, room temperature, and 5 min, 2×SSC, 0.1% SDS, 50° C.

Under these conditions, the probe A enabled us to obtain strong and unambiguous signals; in particular, in the case of the digestions with BamHI, KpnI, SphI, SstI, SmaI, SalI and PstI, a single genomic band was found which hybridized strongly with A, corresponding to the PstI genomic fragment of ≈3.2 kb.

The fragments of 3 to 4 kb from a PstI digestion of the genomic DNA were purified by preparative electrophoresis on agarose and electroelution, and then ligated to plasmid pUC19, itself digested with PstI. After transformation in the strain DH5α, 600 white clones on LB Amp X-gal were subcultured individually and probed by colony hybridization with the probe A under stringency conditions similar to those used in Southern analysis. Nine clones which gave particularly strong hybridization signals were then subjected to a restriction analysis of the plasmid DNA. Among six of these clones which had manifestly inserted the same fragment of ≈3.2 kb in both orientations, two clones representing each of the two orientations (pXL1835 and pXL1836) were analyzed in greater detail (detailed map, Southern analysis), thus confirming that the desired fragment had indeed been obtained.

EXAMPLE 7

Sequence of the PstI Fragment of 3.2 kb

The complete nucleotide sequence of the PstI fragment of 3.2 kb was determined on both strands (see FIG. 14). The GC content of this fragment amounts to 62.4%, i.e. it is of the same order as the content observed in the case of R 312 (≈62%). The analysis of the sequence obtained made it possible to characterize an open reading frame of 1386 nucleotides (position 210 to 1595) coding for a polypeptide of 462 residues (mw 48,554) containing the 3 peptide sequences obtained by sequencing tryptic fragments.

This open reading frame represents the structural gene of the desired enantioselective amidase.

EXAMPLE 8

Homologies Between Different Amidases:

Identification of a Sequence Characteristic of the Amidase Activity

We first compared the peptide sequences of the enantioselective amidases of R 312 with that shown in FIG. 14.

FIG. 16 shows that the two proteins are particularly homologous (strict identity of 50%) in the second third of the sequence, between residues 150 and 300 of R 312, the homology being 67% in the 158–215 region.

We also carried out a search for homologous sequences in the GENPRO bank. This search reveals substantial homologies in the 150–200 region with the sequences of the acetamidase of Aspergillus nidulans, the indolacetamide hydrolase of Pseudomonas syringae and Bradyrhizobium japonicum, the protein tms2 of Agrobacterium tumefaciens and the 6-aminohexanoate cyclic dimer hydrobases (ACDH) of Flavobacterium sp. K172 and Pseudomonas sp. NK87 (See FIG. 17 in particular).

The homology of the peptide 137–193 of the amidase described in the present patent application with the respective sites of these other enzymes (in % strict identity of the amino acids) is given in the following Table:

| AMIDASE | % HOMOLOGY |
| --- | --- |
| R 132 | 65.5 |
| IAH A. tumefaciens | 64.3 |
| IAH P. syringae | 61.8 |
| ACDH (F. or P.) | 61.4 |
| IAH B. japonicum | 54.4 |
| Acetamidase (A. nidulans) | 47.4 |

This region, which is highly conserved, is probably responsive for the activity of these enzymes.

EXAMPLE 9

Expression of the Enantioselective Amidase in *E. coli*

To confirm the identification of the frame coding for an enantioselective amidase, an NdeI site (CATATG) was created by the PCR method at the presumptive ATG in position 210 (FIG. 14) and the fragment between this site and the SalI site (position 1683), containing only the part coding for the amidase, was placed under the control of effective signals for initiating transcription (promoters Ptrp or $P_R$) and translation (RBScII) in *E. coli*. The resulting vectors, pXL1893 (Ptrp) and pXL1894 ($P_RCI^{ts}$), are similar to vectors pXL1752 and pXL1751 described above, expressing the amidase of R 312. The general structure of these expression vectors is reiterated in FIG. 18. The expression from plasmids pXL1893 and pXL1894 was studied in the *E. coli* strains B and K12 E103S respectively. The results obtained in the case of pXL1894 are shown in FIG. 19. A protein comigrating with the purified amidase is specifically produced at 42° C. in the presence of plasmid pXL1894.

EXAMPLE 10

Expression of the Amidase in Corynebacteria

A) Construction of the expression vectors

These vectors are prepared from replicating vectors in *corynebacteria* and comprise:
a replicon of *E. coli*,
a replicon of corynebacterium,
a selection marker and
an Amd sequence.

Vector pSV73 (FIG. 20): This plasmid is derived from vector pSRl of C. glutamicum (Yoshihama et al., J. Bacteriol., 162, 591 (1985)) by insertion of a fragment of plasmid pUC8 containing a replicon of E. coli, and the kanamycin resistance gene originating from transposon Tn903.

Figure 21:
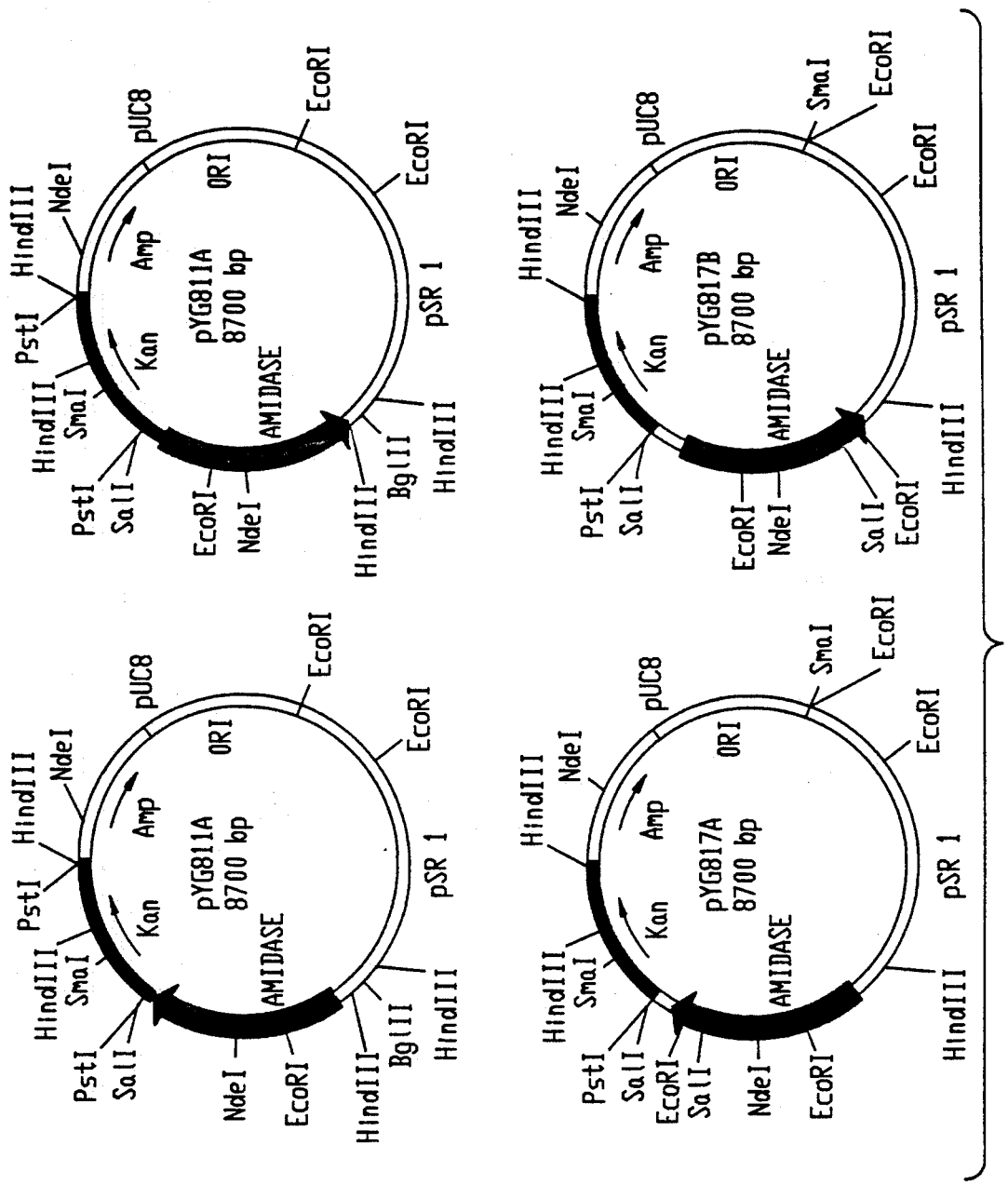

This plasmid was used to construct different vectors for expression of the Amd sequences given in FIGS. 14 and 15, especially:

Vectors pYG811A and B (FIG. 21): These vectors are derived from vector pSV73 by cloning at the SalI site, in both orientations, of the Amd sequence given in FIG. 14.

Vectors pYG817A and B (FIG. 21): These vectors are derived from vector pSV73 by cloning at the BglII site, in both orientations, of the Amd sequence given in FIG. 14.

Vector pYG822 (FIG. 20): This vector is derived from pSV73 by cloning at the SalI-BglII sites of an expression cassette containing the Amd sequence of FIG. 14 and bacteriophage lambda promoter Ptrp.

Other cryptic plasmids of corynebacterium can also be used to construct vectors for expression of Amd sequences in corynebacteria. In particular, plasmid pX18, isolated from B. lactofermentum (Yoshihama et al., op. cit.), made it possible to construct shuttle vector pYG820A, whose restriction map is given in FIG. 20.

B) Transformation of the corynebacteria

All the techniques known to those skilled in the art can be used, especially the protoplastization-regeneration technique described by Yoshihama et al., op. cit. However, the Applicant has shown that the electroporation technique is very advantageous since it enables the transformation frequency to be increased up to 1000-fold.

The analysis of the supernatants of sonicated and centrifuged cultures in polyacrylamide-SDS indicates the presence of transformants.

EXAMPLE 11

Enzymic Catalysis

This Example illustrates the use, according to the invention, of the polypeptides or recombinant microorganisms prepared in the previous Examples in the synthesis of ammonium adipate by the hydrolysis of adipamide or ammonium adipamate.

A) Culture media for the strains used

1—for the natural strains

| Medium 1: for Brevibacterium R 312 | |
|---|---|
| glucose | 10 g/l |
| $(NH_4)_2SO_4$ | 5 g/l |
| $KH_2PO_4$ | 1.01 g/l |
| $Na_2HPO_4.12H_2O$ | 1.64 g/l |
| $K_2HPO_4$ | 0.82 g/l |
| $CaCl_2.2H_2O$ | 0.012 g/l |
| $ZnCl_2$ | 0.0012 g/l |
| $FeSO_4.7H_2O$ | 0.0012 g/l |
| $MnSO_4.H_2O$ | 0.0012 g/l |
| $MgSO_4.7H_2O$ | 0.5 g/l |
| thiamine hydrochloride | 0.002 g/l |
| distilled water | |
| Medium 2: for Rhodococcus | |
| glycerol | 5 g/l |
| yeast extract (Difco) | 1 g/l |
| beef extract (Difco) | 1 g/l |
| $K_2HPO_4$ | 2 g/l |
| $MgSO_4.7H_2O$ | 0.5 g/l |
| $FeSO_4.7H_2O$ | 20 mg/l |
| $MnSO_4.H_2O$ | 20 mg/l |
| NaCl | 10 mg/l |
| mineral solution* | 10 mg/l |
| NaOH q.s. pH | 7.2 |
| isobutyronitrile | 5 g/l |
| * mineral solution: | |
| $CaCl_2.2H_2O$ | 200 mg/l |
| $Na_2MoO_4.2H_2O$ | 15 mg/l |
| $ZnSO_4.7H_2O$ | 4 mg/l |
| $CuSO_4.5H_2O$ | 0.4 mg/l |
| $CoCl_2.4H_2O$ | 0.4 mg/l |
| $H_3BO_3$ | 20 mg/l |
| KI | 10 mg/l |
| HCl 10% | 10 mg/l |

2—for the recombinant strains

| Medium 3: | |
|---|---|
| NaCl | 5 g/l |
| Bacto-tryptone | 10 g/l |
| yeast extract | 5 g/l |
| isobutyronitrile | 5 g/l |
| kanamycin | 1 g/l |
| Medium 4: | |
| NaCl | 5 g/l |
| Bacto-tryptone | 10 g/l |
| yeast extract | 5 g/l |
| isobutyronitrile | 2.5 g/l |
| isobutyramide | 2.5 g/l |
| kanamycin | 20 mg/l |
| Medium 5: | |
| $Na_2HPO_4$ | 7 g/l |
| $KH_2PO_4$ | 3 g/l |
| NaCl | 0.5 g/l |
| $NH_4Cl$ | 1 g/l |
| thiamine hydrochloride | 0.01 g/l |
| glucose | 4 g/l |
| $MgSO_4$ | 1 mM |
| $CaCl_2$ | 0.1 mM |
| ampicillin | 100 μg/ml |
| Medium 6: | |

-continued

| | |
|---|---|
| medium 5 | |
| tryptophan | 40 mg/l |

B) Preparation of the cell residues

The cultures of the various strains are carried out in 2-liter conical flasks filled with 600 ml of medium, at 30° C., on a shaking table (150 vibrations/min). When culture has ended, the cells are harvested, washed with isotonic solution, divided up into Eppentubes and kept at −18° C. until used. The media and the characteristics of the cultures of the various strains tested are given in Table I below.

C) Measurement of the amidase activity

The protocol is as follows:

The adipamide or ammonium adipamate, the cell suspension and 50 mM potassium phosphate buffer, pH 7.0, are introduced into a flask equipped with a stirrer.

The stoppered flask is placed in a crystallizing dish thermostated at 25° C., with stirring throughout the reaction.

The reaction medium is then diluted with 0.1 N hydrochloric acid.

The bacteria and cell debris are removed by centrifugation followed by filtration (0.45 μm).

The composition in terms of adipic acid, adipamide and/or adipamic acid is determined by HPLC.

The results obtained and the loadings used are given in Table II below.

In this Table:
W = whole cell
S = sonicated cell
IBN = isobutyronitrile
IBAm = isobutyramide
NMA = N-methylacetamide
Thp = tryptophan -= none

TABLE I

Media and characteristics of the cultures of the various strains tested

| Strain | Medium | OD 660 | Solids g/l | Protein g/l |
|---|---|---|---|---|
| Brevibacterium R 312 | 1 | 2.1 | 1.5 | 0.35 |
| E. coli (pXL906) | 5 | 2.3 | 1.1 | 0.49 |
| E. coli (pXL1751) | 5 | 1.5 | 0.8 | 0.4 |
| E. coli (pXL1751) | 6 | 2.7 | 1.4 | 0.4 |
| Rhodococcus | 2 | 3.1 | 1.1 | 0.27 |
| Brevibacterium R 312 (pSV73) | 3 | 2.5 | 2.1 | 0.32 |
| Brevibacterium R 312 (pYG811A) | 3 | 3.2 | 2.5 | 0.5 |
| Brevibacterium R 312 (pYG811B) | 3 | 2 | 1.3 | 0.27 |
| Brevibacterium lactofermentum (pSV73) | 4 | 3.1 | 2.0 | 0.30 |
| Brevibacterium lactofermentum (pYG822) | 4 | 3.1 | 1.9 | 0.29 |

TABLE II

Loadings, reaction conditions and results of the measurement of the amidase activity on adipamide and adipamate

| MICROORGANISM | | | SUBSTRATE | | CELLS | VOLUME | DURATION | ACTIVITY |
|---|---|---|---|---|---|---|---|---|
| Nature | Effector substance | State | Nature | μmol | mg of protein | (ml) | (h) | (μmol/h/mg of protein) |
| Brevibacterium R 312 | NMA | W | Adipamide | 100 | 0.3 | 5 | 15 | 0.6 |
| idem | idem | S | idem | 100 | 1.6 | 5 | 15 | 2.6 |
| idem | idem | W | Adipamide | 100 | 0.3 | 5 | 15 | 0 |
| idem | idem | S | idem | 100 | 1.6 | 5 | 15 | 1.1 |
| E. coli (pXL906) | — | W | Adipamide | 100 | 1.6 | 5 | 15 | 0 |
| idem | — | S | idem | 100 | 1.6 | 5 | 15 | 0 |
| idem | — | W | Adipamide | 100 | 1.6 | 5 | 15 | 0 |
| idem | — | S | idem | 100 | 1.6 | 5 | 15 | 0 |
| E. coli (pXL1751) | Thp | W | Adipamide | 90 | 1.6 | 5 | 15 | 1.5 |
| idem | idem | S | idem | 95 | 1.6 | 5 | 15 | 2.2 |
| idem | idem | W | Adipamide | 105 | 1.6 | 5 | 15 | 0.3 |
| idem | idem | S | idem | 105 | 1.6 | 5 | 15 | 0.6 |
| E. coli (pXL1751) | — | W | Adipamide | 95 | 1.6 | 5 | 15 | 9 |
| idem | — | S | idem | 85 | 1.6 | 5 | 15 | >2.6 |
| idem | — | W | Adipamide | 95 | 1.6 | 5 | 15 | 2 |
| idem | — | S | idem | 95 | 1.6 | 5 | 15 | 1.9 |
| Rhodococcus | IBN | W | Adipamide | 500 | 19 | 25 | 3 | 8.4 |
| idem | idem | S | idem | 500 | 19 | 25 | 3 | 15 |
| idem | idem | W | Adipamide | 500 | 8 | 25 | 14 | 0 |
| idem | idem | S | idem | 500 | 8 | 25 | 15 | 13.4 |
| Brevibacterium R 312 (pSV73) | IBN | W | Adipamide | 100 | 1.6 | 5 | 15 | 0.4 |
| Brevibacterium R 312 (pYG811A) | IBN | W | Adipamide | 100 | 1.6 | 5 | 15 | 3.6 |
| Brevibacterium R 312 (pYG811B) | IBN | W | Adipamide | 100 | 1.6 | 5 | 15 | 3.5 |
| Brevibacterium lactofermentum (pSV73) | − −IBN + − −I-BAm | W | Adipamide | 100 | 1.6 | 5 | 15 | 0 |
| Brevibacterium lactofermentum (pYG822) | − −IBN + − −I-BAm | W | Adipamide | 100 | 1.6 | 5 | 15 | 2.3 |

SEQUENCE LISTING ( 1 ) GENERAL INFORMATION:

( i i i ) NUMBER OF SEQUENCES: 24

( 2 ) INFORMATION FOR SEQ ID NO:1:

( i ) SEQUENCE CHARACTERISTICS:
　　　　( A ) LENGTH: 27 amino acids
　　　　( B ) TYPE: amino acid
　　　　( D ) TOPOLOGY: linear ( i i ) MOLECULE TYPE: peptide ( v ) FRAGMENT TYPE: N-terminal ( x i ) SEQUENCE DESCRIPTION: SEQ ID NO:1:

Ala Thr Ile Arg Pro Asp Asp Lys Ala Ile Asp Ala Ala Ala Arg His
1               5                   10                  15

Tyr Gly Ile Thr Leu Asp Lys Thr Ala Arg Leu
            20                  25

( 2 ) INFORMATION FOR SEQ ID NO:2:

( i ) SEQUENCE CHARACTERISTICS:
　　　　( A ) LENGTH: 21 amino acids
　　　　( B ) TYPE: amino acid
　　　　( D ) TOPOLOGY: linear ( i i ) MOLECULE TYPE: peptide ( v ) FRAGMENT TYPE: internal ( x i ) SEQUENCE DESCRIPTION: SEQ ID NO:2:

Leu Glu Trp Pro Ala Leu Ile Asp Gly Ala Leu Gly Ser Tyr Asp Val
1               5                   10                  15

Val Asp Gln Leu Tyr
            20

( 2 ) INFORMATION FOR SEQ ID NO:3:

( i ) SEQUENCE CHARACTERISTICS:
　　　　( A ) LENGTH: 29 base pairs
　　　　( B ) TYPE: nucleic acid
　　　　( C ) STRANDEDNESS: double
　　　　( D ) TOPOLOGY: linear ( i i ) MOLECULE TYPE: DNA (genomic)

( x i ) SEQUENCE DESCRIPTION: SEQ ID NO:3:

ATCGATGGCG CCCTCGGCTC CTACGATGT                                         29

( 2 ) INFORMATION FOR SEQ ID NO:4:

( i ) SEQUENCE CHARACTERISTICS:
　　　　( A ) LENGTH: 10 amino acids
　　　　( B ) TYPE: amino acid
　　　　( D ) TOPOLOGY: linear ( i i ) MOLECULE TYPE: peptide ( x i ) SEQUENCE DESCRIPTION: SEQ ID NO:4:

Ile Asp Gly Ala Leu Gly Ser Tyr Asp Val
1               5                   10

( 2 ) INFORMATION FOR SEQ ID NO:5:

( i ) SEQUENCE CHARACTERISTICS:
　　　　( A ) LENGTH: 62 base pairs
　　　　( B ) TYPE: nucleic acid
　　　　( C ) STRANDEDNESS: double
　　　　( D ) TOPOLOGY: linear ( i i ) MOLECULE TYPE: DNA (genomic)

( i x ) FEATURE:
    ( A ) NAME/KEY: CDS
    ( B ) LOCATION: complement (9..62)

( x i ) SEQUENCE DESCRIPTION: SEQ ID NO:5:

```
AAGCTTGCTG TTTTGTCAAG CGTGATGCCG TAATGCCTTG CGGCGGCGTC TATTGCTTTG        60
TC                                                                       62
```

( 2 ) INFORMATION FOR SEQ ID NO:6:

( i ) SEQUENCE CHARACTERISTICS:
        ( A ) LENGTH: 18 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Asp Lys Ala Ile Asp Ala Ala Ala Arg His Tyr Gly Ile Thr Leu Asp
 1               5                  10                  15
Lys Thr
```

( 2 ) INFORMATION FOR SEQ ID NO:7:

( i ) SEQUENCE CHARACTERISTICS:
        ( A ) LENGTH: 24 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: complement (1..18)

( i x ) FEATURE:
        ( A ) NAME/KEY: unsure
        ( B ) LOCATION: 19..24
        ( D ) OTHER INFORMATION: /note="The sequence of this region
            was determined on the basis of the sequence of the
            complimentary strand."

( x i ) SEQUENCE DESCRIPTION: SEQ ID NO:7:

```
GTCTGGTCGA ATGGTATCGA ATTC                                               24
```

( 2 ) INFORMATION FOR SEQ ID NO:8:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

```
Asp Thr Ile Arg Pro Asp
 1               5
```

( 2 ) INFORMATION FOR SEQ ID NO:9:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

```
GATGCGGTAA TGCCTTGCGG CGGCGTCTAT TGCTTTGTCG                                40
```

( 2 ) INFORMATION FOR SEQ ID NO:10:

( i ) SEQUENCE CHARACTERISTICS:
        ( A ) LENGTH: 1879 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 245..1807

( x i ) SEQUENCE DESCRIPTION: SEQ ID NO:10:

```
CGATCCGGAA ACAGTACTTC GGCAGCTTGC CACGACACCG AAAAGCTCTA CGAACACCGG          60

TGTTCCACTG CATCGGCCGA TTCTGATCGC TGAATCGGCC CGTGGGCGAC TGTACCCCCG         120

CTCTCTCTGA GCGCACGTAA CCCGAACTTA ACGAGTCAAT ATGTCGATAC CTATTGACGC         180

AATTATGGAT CCGGCCCTAG TCTGAAAGAC AAGTGAAGCC GATCACATCA GGAGCACACT         240

TCTC ATG GCG ACA ATC CGA CCT GAC GAC AAA GCA ATA GAC GCC GCC GCA          289
     Met Ala Thr Ile Arg Pro Asp Asp Lys Ala Ile Asp Ala Ala Ala
     1               5                  10                    15

AGG CAT TAC GGC ATC ACT CTC GAC AAA ACA GCC CGG CTC GAG TGG CCG           337
Arg His Tyr Gly Ile Thr Leu Asp Lys Thr Ala Arg Leu Glu Trp Pro
                 20                  25                  30

GCA CTG ATC GAC GGA GCA CTG GGC TCC TAC GAC GTC GTC GAC CAG TTG           385
Ala Leu Ile Asp Gly Ala Leu Gly Ser Tyr Asp Val Val Asp Gln Leu
             35                  40                  45

TAC GCC GAC GAG GCG ACC CCG CCG ACC ACG TCA CGC GAG CAC GCG GTG           433
Tyr Ala Asp Glu Ala Thr Pro Pro Thr Thr Ser Arg Glu His Ala Val
         50                  55                  60

CCA AGT GCG AGC GAA AAT CCT TTG AGC GCT TGG TAT GTG ACC ACC AGC           481
Pro Ser Ala Ser Glu Asn Pro Leu Ser Ala Trp Tyr Val Thr Thr Ser
     65                  70                  75

ATC CCG CCG ACG TCG GAC GGC GTC CTG ACC GGC CGA CGC GTG GCG ATC           529
Ile Pro Pro Thr Ser Asp Gly Val Leu Thr Gly Arg Arg Val Ala Ile
80                  85                  90                  95

AAG GAC AAC GTG ACC GTG GCC GGA GTT CCG ATG ATG AAC GGA TCT CGG           577
Lys Asp Asn Val Thr Val Ala Gly Val Pro Met Met Asn Gly Ser Arg
                    100                 105                 110

ACG GTA GAG GGA TTT ACT CCG TCA CGC GAC GCG ACT GTG GTC ACT CGA           625
Thr Val Glu Gly Phe Thr Pro Ser Arg Asp Ala Thr Val Val Thr Arg
                115                 120                 125

CTA CTG GCG GCC GGT GCA ACC GTC GCG GGC AAA GCT GTG TGT GAG GAC           673
Leu Leu Ala Ala Gly Ala Thr Val Ala Gly Lys Ala Val Cys Glu Asp
            130                 135                 140

CTG TGT TTC TCC GGT TCG AGC TTC ACA CCG GCA AGC GGA CCG GTC CGC           721
Leu Cys Phe Ser Gly Ser Ser Phe Thr Pro Ala Ser Gly Pro Val Arg
        145                 150                 155

AAT CCA TGG GAC CGG CAG CGC GAA GCA GGT GGA TCA TCC GGC GGG AGT           769
Asn Pro Trp Asp Arg Gln Arg Glu Ala Gly Gly Ser Ser Gly Gly Ser
160                 165                 170                 175

GCA GCA CTC GTC GCA AAC GGT GAC GTC GAT TTT GCC ATC GGC GGG GAT           817
Ala Ala Leu Val Ala Asn Gly Asp Val Asp Phe Ala Ile Gly Gly Asp
                    180                 185                 190

CAA GGC GGA TCG ATC CGG ATC CCG GCG GCA TTC TGC GGC GTC GTC GGG           865
Gln Gly Gly Ser Ile Arg Ile Pro Ala Ala Phe Cys Gly Val Val Gly
                195                 200                 205

CAC AAG CCG ACG TTC GGG CTC GTC CCG TAT ACC GGT GCA TTT CCC ATC           913
```

|     |     |     |     |     |     |     |     |     |     |     |     |     |     |     |     |     |
|-----|-----|-----|-----|-----|-----|-----|-----|-----|-----|-----|-----|-----|-----|-----|-----|-----|
| His | Lys | Pro | Thr | Phe | Gly | Leu | Val | Pro | Tyr | Thr | Gly | Ala | Phe | Pro | Ile |     |
|     |     | 210 |     |     |     |     | 215 |     |     |     | 220 |     |     |     |     |     |

```
GAG  CGA  ACA  ATC  GAC  CAT  CTC  GGC  CCG  ATC  ACA  CGC  ACG  GTC  CAC  GAT          961
Glu  Arg  Thr  Ile  Asp  His  Leu  Gly  Pro  Ile  Thr  Arg  Thr  Val  His  Asp
     225                      230                     235

GCA  GCA  CTG  ATG  CTC  TCG  GTC  ATC  GCC  GGC  CGC  GAC  GGT  AAC  GAC  CCA         1009
Ala  Ala  Leu  Met  Leu  Ser  Val  Ile  Ala  Gly  Arg  Asp  Gly  Asn  Asp  Pro
240                      245                     250                          255

CGC  CAA  GCC  GAC  AGT  GTC  GAA  GCA  GGT  GAC  TAT  CTG  TCC  ACC  CTC  GAC         1057
Arg  Gln  Ala  Asp  Ser  Val  Glu  Ala  Gly  Asp  Tyr  Leu  Ser  Thr  Leu  Asp
                    260                      265                     270

TCC  GAT  GTG  GAC  GGC  CTG  CGA  ATC  GGA  ATC  GTT  CGA  GAG  GGA  TCC  GGG         1105
Ser  Asp  Val  Asp  Gly  Leu  Arg  Ile  Gly  Ile  Val  Arg  Glu  Gly  Ser  Gly
               275                      280                     285

CAC  GCG  CTC  TCA  CAG  CCC  GAG  GTC  GAC  GAC  GCA  GTC  CGC  GCA  GCG  GCA         1153
His  Ala  Leu  Ser  Gln  Pro  Glu  Val  Asp  Asp  Ala  Val  Arg  Ala  Ala  Ala
          290                      295                     300

CAC  AGT  CTG  ACC  GAA  ATC  GGT  TGC  ACG  GTA  GAG  GAA  GTA  AAC  ATC  CCG         1201
His  Ser  Leu  Thr  Glu  Ile  Gly  Cys  Thr  Val  Glu  Glu  Val  Asn  Ile  Pro
     305                      310                     315

TGG  CAT  CTG  CAT  GCT  TTC  CAC  ATC  TGG  AAC  GTG  ATC  GCC  ACG  GAC  GGT         1249
Trp  His  Leu  His  Ala  Phe  His  Ile  Trp  Asn  Val  Ile  Ala  Thr  Asp  Gly
320                      325                     330                          335

GGT  GCC  TAC  CAG  ATG  TTG  GAC  GGC  AAC  GGA  TAC  GGC  ATG  AAC  GCC  GAA         1297
Gly  Ala  Tyr  Gln  Met  Leu  Asp  Gly  Asn  Gly  Tyr  Gly  Met  Asn  Ala  Glu
                    340                      345                     350

GGT  TTG  TAC  GAT  CCG  GAA  CTG  ATG  GCA  CAC  TTT  GCT  TCT  CGA  CGC  ATT         1345
Gly  Leu  Tyr  Asp  Pro  Glu  Leu  Met  Ala  His  Phe  Ala  Ser  Arg  Arg  Ile
               355                      360                     365

CAG  CAC  GCC  GAC  GCT  CTG  TCC  GAA  ACC  GTC  AAA  CTG  GTG  GCC  CTG  ACC         1393
Gln  His  Ala  Asp  Ala  Leu  Ser  Glu  Thr  Val  Lys  Leu  Val  Ala  Leu  Thr
          370                      375                     380

GGC  CAC  CAC  GGC  ATC  ACC  ACC  CTC  GGC  GGC  GCG  AGC  TAC  GGC  AAA  GCC         1441
Gly  His  His  Gly  Ile  Thr  Thr  Leu  Gly  Gly  Ala  Ser  Tyr  Gly  Lys  Ala
     385                      390                     395

CGG  AAC  CTC  GTA  CCG  CTT  GCC  CGC  GCC  GCC  TAC  GAC  ACT  GCC  TTG  AGA         1489
Arg  Asn  Leu  Val  Pro  Leu  Ala  Arg  Ala  Ala  Tyr  Asp  Thr  Ala  Leu  Arg
400                      405                     410                          415

CAA  TTC  GAC  GTC  CTG  GTG  ATG  CCA  ACG  CTG  CCC  TAC  GTC  GCA  TCC  GAA         1537
Gln  Phe  Asp  Val  Leu  Val  Met  Pro  Thr  Leu  Pro  Tyr  Val  Ala  Ser  Glu
                    420                      425                     430

TTG  CCG  GCG  AAG  GAC  GTA  GAT  CGT  GCA  ACC  TTC  ATC  ACC  AAG  GCT  CTC         1585
Leu  Pro  Ala  Lys  Asp  Val  Asp  Arg  Ala  Thr  Phe  Ile  Thr  Lys  Ala  Leu
               435                      440                     445

GGG  ATG  ATC  GCC  AAC  ACG  GCA  CCA  TTC  GAC  GTG  ACC  GGA  CAT  CGC  TCC         1633
Gly  Met  Ile  Ala  Asn  Thr  Ala  Pro  Phe  Asp  Val  Thr  Gly  His  Arg  Ser
          450                      455                     460

CTG  TCC  GTT  CCG  GCC  GGC  CTG  GTG  AAC  GGG  CCT  CCG  GTC  GGA  ATG  ATG         1681
Leu  Ser  Val  Pro  Ala  Gly  Leu  Val  Asn  Gly  Pro  Pro  Val  Gly  Met  Met
     465                      470                     475

ATC  ACC  GGC  AGA  CAC  TTC  GAC  GAT  GCG  ACA  GCT  CTT  CGT  GTC  GGA  CGC         1729
Ile  Thr  Gly  Arg  His  Phe  Asp  Asp  Ala  Thr  Ala  Leu  Arg  Val  Gly  Arg
480                      485                     490                          495

GCA  TTC  GAA  AAC  CCT  CGC  GGC  GCG  TTT  CCG  ACG  CCG  GCC  GAA  CGC  GCC         1777
Ala  Phe  Glu  Asn  Pro  Arg  Gly  Ala  Phe  Pro  Thr  Pro  Ala  Glu  Arg  Ala
                    500                      505                     510

TCC  AAC  TCT  GCA  CCA  CAA  CTC  AGC  CCC  GCC  TAGTCCTGAC  GCACTGTCAG              1827
Ser  Asn  Ser  Ala  Pro  Gln  Leu  Ser  Pro  Ala
               515                      520

ACAACAAATT  CCACCGATTC  ACACATGATC  AGCCCACATA  AGAAAAGGTG  AA                        1879
```

( 2 ) INFORMATION FOR SEQ ID NO:11:

( i ) SEQUENCE CHARACTERISTICS:
        ( A ) LENGTH: 521 amino acids
        ( B ) TYPE: amino acid
        ( D ) TOPOLOGY: linear ( i i ) MOLECULE TYPE: protein ( x i ) SEQUENCE DESCRIPTION: SEQ ID NO:11:

```
Met Ala Thr Ile Arg Pro Asp Asp Lys Ala Ile Asp Ala Ala Arg
  1           5                  10                  15

His Tyr Gly Ile Thr Leu Asp Lys Thr Ala Arg Leu Glu Trp Pro Ala
             20                  25                  30

Leu Ile Asp Gly Ala Leu Gly Ser Tyr Asp Val Val Asp Gln Leu Tyr
             35                  40                  45

Ala Asp Glu Ala Thr Pro Pro Thr Thr Ser Ala Glu His Ala Val Pro
 50                   55                  60

Ser Ala Ser Glu Asn Pro Leu Ser Ala Trp Tyr Val Thr Thr Ser Ile
 65              70                   75                      80

Pro Pro Thr Ser Asp Gly Val Leu Thr Gly Arg Arg Val Ala Ile Lys
                 85                  90                  95

Asp Asn Val Thr Val Ala Gly Val Pro Met Met Asn Gly Ser Arg Thr
             100                 105                 110

Val Glu Gly Phe Thr Pro Ser Arg Asp Ala Thr Val Val Thr Arg Leu
             115                 120                 125

Leu Ala Ala Gly Ala Thr Val Ala Gly Lys Ala Val Cys Glu Asp Leu
 130                 135                 140

Cys Phe Ser Gly Ser Ser Phe Thr Pro Ala Ser Gly Pro Val Arg Asn
145                  150                 155                 160

Pro Trp Asp Arg Gln Arg Glu Ala Gly Gly Ser Ser Gly Gly Ser Ala
                 165                 170                 175

Ala Leu Val Ala Asn Gly Asp Val Asp Phe Ala Ile Gly Gly Asp Gln
             180                 185                 190

Gly Gly Ser Ile Arg Ile Pro Ala Ala Phe Cys Gly Val Val Gly His
             195                 200                 205

Lys Pro Thr Phe Gly Leu Val Pro Tyr Thr Gly Ala Phe Pro Ile Glu
210                  215                 220

Arg Thr Ile Asp His Leu Gly Pro Ile Thr Arg Thr Val His Asp Ala
225                  230                 235                 240

Ala Leu Met Leu Ser Val Ile Ala Gly Arg Asp Gly Asn Asp Pro Arg
                 245                 250                 255

Gln Ala Asp Ser Val Glu Ala Gly Asp Tyr Leu Ser Thr Leu Asp Ser
             260                 265                 270

Asp Val Asp Gly Leu Arg Ile Gly Ile Val Arg Glu Gly Phe Gly His
             275                 280                 285

Ala Val Ser Gln Pro Glu Val Asp Asp Ala Val Arg Ala Ala Ala His
290                  295                 300

Ser Leu Thr Glu Ile Gly Cys Thr Val Glu Glu Val Asn Ile Pro Trp
305                  310                 315                 320

His Leu His Ala Phe His Ile Trp Asn Val Ile Ala Thr Asp Gly Gly
                 325                 330                 335

Ala Tyr Gln Met Leu Asp Gly Asn Gly Tyr Gly Met Asn Ala Glu Gly
             340                 345                 350

Leu Tyr Asp Pro Glu Leu Met Ala His Phe Ala Ser Arg Arg Ile Gln
             355                 360                 365

His Ala Asp Ala Leu Ser Glu Thr Val Lys Leu Val Ala Leu Thr Gly
370                  375                 380
```

| His | His | Gly | Ile | Thr | Thr | Leu | Gly | Gly | Ala | Ser | Tyr | Gly | Lys | Ala | Arg |
| 385 | | | | 390 | | | | | 395 | | | | | | 400 |

| Asn | Leu | Val | Pro | Leu | Ala | Arg | Ala | Ala | Tyr | Asp | Thr | Ala | Leu | Arg | Gln |
| | | | 405 | | | | | 410 | | | | | 415 | | |

| Phe | Asp | Val | Leu | Val | Met | Pro | Thr | Leu | Pro | Tyr | Val | Ala | Ser | Glu | Leu |
| | | | 420 | | | | 425 | | | | | 430 | | | |

| Pro | Ala | Lys | Asp | Val | Asp | Arg | Ala | Thr | Phe | Ile | Thr | Lys | Ala | Leu | Gly |
| | | 435 | | | | | 440 | | | | | 445 | | | |

| Met | Ile | Ala | Asn | Thr | Ala | Pro | Phe | Asp | Val | Thr | Gly | His | Pro | Ser | Leu |
| | 450 | | | | | 455 | | | | | 460 | | | | |

| Ser | Val | Pro | Ala | Gly | Leu | Val | Asn | Gly | Leu | Pro | Val | Gly | Met | Met | Ile |
| 465 | | | | | 470 | | | | | 475 | | | | | 480 |

| Thr | Gly | Arg | His | Phe | Asp | Asp | Ala | Thr | Val | Leu | Arg | Val | Gly | Arg | Ala |
| | | | | 485 | | | | | 490 | | | | | 495 | |

| Phe | Glu | Lys | Leu | Arg | Gly | Ala | Phe | Pro | Thr | Pro | Ala | Glu | Arg | Ala | Ser |
| | | | 500 | | | | | 505 | | | | | 510 | | |

| Asn | Ser | Ala | Pro | Gln | Leu | Ser | Pro | Ala |
| | | 515 | | | | | 520 | |

( 2 ) INFORMATION FOR SEQ ID NO:12:

( i ) SEQUENCE CHARACTERISTICS:
        ( A ) LENGTH: 1640 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 210..1598

( x i ) SEQUENCE DESCRIPTION: SEQ ID NO:12:

```
CTGCAGAACG GAACTAAGAT GGCTCGAACC TTCACCAAAG ACGGACTTGA ACACAGCCTC        60

GCACTTGCGC GTTTGGAGCT CCCGGACGAG CGTTACGAGA CGGTGACAGC GGCTGCCGAG       120

TTGGTCCTCG GACTCGCTGA GGCTCTGGAT GCTGTCCCGC TGGCCGAGAC TCCGATGGCA       180

GCCGCCTTCG ATGCGCGGTG GGAGTGACG ATG GGC TTG CAT GAA CTG ACG CTC        233
                                  Met Gly Leu His Glu Leu Thr Leu
                                   1               5
```

| GCG | CAA | GTC | GCT | GCG | AAG | ATC | GAG | AAC | AAA | GAA | CTT | TCC | CCG | GTC | GAG | 281 |
| Ala | Gln | Val | Ala | Ala | Lys | Ile | Glu | Asn | Lys | Glu | Leu | Ser | Pro | Val | Glu | |
| | 10 | | | | | 15 | | | | | 20 | | | | | |

| CTC | CTC | GAT | GTG | ATC | CTG | GCG | CGC | GTC | GCG | GAG | ATC | GAA | CCG | AAG | ATC | 329 |
| Leu | Leu | Asp | Val | Ile | Leu | Ala | Arg | Val | Ala | Glu | Ile | Glu | Pro | Lys | Ile | |
| 25 | | | | | 30 | | | | | 35 | | | | | 40 | |

| TCC | GCC | TTC | GTC | ACG | ATC | ACC | GCC | GAT | TCC | GCT | CGG | AAG | GCG | GCC | CGG | 377 |
| Ser | Ala | Phe | Val | Thr | Ile | Thr | Ala | Asp | Ser | Ala | Arg | Lys | Ala | Ala | Arg | |
| | | | | 45 | | | | | 50 | | | | | 55 | | |

| CTC | GCA | GCC | GAC | GAG | ATC | GCA | GGT | GGG | CAC | TAT | CGC | GGT | CCG | CTG | CAC | 425 |
| Leu | Ala | Ala | Asp | Glu | Ile | Ala | Gly | Gly | His | Tyr | Arg | Gly | Pro | Leu | His | |
| | | | 60 | | | | | 65 | | | | | 70 | | | |

| GGA | GTT | CCG | ATT | GGC | CTC | AAG | GAT | CTG | TTC | GAA | GTG | GCA | GGC | GTC | CCG | 473 |
| Gly | Val | Pro | Ile | Gly | Leu | Lys | Asp | Leu | Phe | Glu | Val | Ala | Gly | Val | Pro | |
| | | 75 | | | | | 80 | | | | | 85 | | | | |

| AAT | ACC | GCG | AGT | TCG | CGG | GTC | CGA | GCT | GAC | TAC | ATC | CCC | TCA | TCG | GAT | 521 |
| Asn | Thr | Ala | Ser | Ser | Arg | Val | Arg | Ala | Asp | Tyr | Ile | Pro | Ser | Ser | Asp | |
| | 90 | | | | | 95 | | | | | 100 | | | | | |

| GGG | GCC | GCG | GTC | GAG | AAG | CTC | ACC | GCC | GGT | GGA | GCG | GTC | ATG | ATC | GGC | 569 |
| Gly | Ala | Ala | Val | Glu | Lys | Leu | Thr | Ala | Gly | Gly | Ala | Val | Met | Ile | Gly | |

|     | 105 |     |     |     | 110 |     |     |     | 115 |     |     |     | 120 |     |     |     |      |
|-----|-----|-----|-----|-----|-----|-----|-----|-----|-----|-----|-----|-----|-----|-----|-----|-----|------|
| AAG | ACG | CAC | ACT | CAC | GAA | TTC | GCC | TAC | GGT | GCG | ATC | ACA | CCG | ACC | ACC |     | 617  |
| Lys | Thr | His | Thr | His | Glu | Phe | Ala | Tyr | Gly | Ala | Ile | Thr | Pro | Thr | Thr |     |      |
|     |     |     |     | 125 |     |     |     |     | 130 |     |     |     |     | 135 |     |     |      |

```
CGT AAT CCA TGG GAC CCC ACC CGG ACA CCC GGC GGT TCC AGC GGT GGG     665
Arg Asn Pro Trp Asp Pro Thr Arg Thr Pro Gly Gly Ser Ser Gly Gly
            140                 145                 150

ACG GCA GCA GCT CTC GCG GCA GGC CTC ATC TTC GCC GGT ATG GGT ACC     713
Thr Ala Ala Ala Leu Ala Ala Gly Leu Ile Phe Ala Gly Met Gly Thr
            155                 160                 165

GAT ACC GGG GGG TCC ATT CGG ATA CCA GCC GCC GTC TGC GGG ACG GTA     761
Asp Thr Gly Gly Ser Ile Arg Ile Pro Ala Ala Val Cys Gly Thr Val
            170                 175                 180

GGT CTC AAA CCC ACA TAT GGT CGC GTT TCG CGT CGT GGA GTG ACC TCC     809
Gly Leu Lys Pro Thr Tyr Gly Arg Val Ser Arg Arg Gly Val Thr Ser
185             190                 195                 200

TTG TCA TGG TCT CTG GAC CAC GCG GGA CCG CTG GCC CGG ACC GTG GAA     857
Leu Ser Trp Ser Leu Asp His Ala Gly Pro Leu Ala Arg Thr Val Glu
                    205                 210                 215

GAC GCT GCC ATC ATG CTG AAC CAG ATC GCT GGC TAT GAC CGG GCT GAT     905
Asp Ala Ala Ile Met Leu Asn Gln Ile Ala Gly Tyr Asp Arg Ala Asp
                    220                 225                 230

CCT GCG ACG GTA GAT GTG CCC GTT CCC GAC TAC GCG GCG GCG CTG ACC     953
Pro Ala Thr Val Asp Val Pro Val Pro Asp Tyr Ala Ala Ala Leu Thr
                235                 240                 245

GGA GAC GTC CGA GGG CTG CGG ATT GGT GTG CCG ACC AAT TTC TAC ACC    1001
Gly Asp Val Arg Gly Leu Arg Ile Gly Val Pro Thr Asn Phe Tyr Thr
250                 255                 260

GAC AAC GTC CAT CCC GAG GTT GCC GCA GCG GCC GAC GCT GCG GTG GCG    1049
Asp Asn Val His Pro Glu Val Ala Ala Ala Ala Asp Ala Ala Val Ala
265                 270                 275                 280

CAA CTG GCC CAT TTG GGT GCG GTG GTC CGC GAA GTG AAG ATC CCG ATG    1097
Gln Leu Ala His Leu Gly Ala Val Val Arg Glu Val Lys Ile Pro Met
                285                 290                 295

GCA GAG GTC ATC GTG CCC ACC GAG TGG AGC TTG CTC GTC CCG GAG GCG    1145
Ala Glu Val Ile Val Pro Thr Glu Trp Ser Leu Leu Val Pro Glu Ala
                300                 305                 310

TCG GCC TAC CAC CAG CAG ATG CTG CGC GAG CGC GCA GAT CAC TAC ACC    1193
Ser Ala Tyr His Gln Gln Met Leu Arg Glu Arg Ala Asp His Tyr Thr
            315                 320                 325

GAC GAG ACG AGA ACC TTC CTG GAA GCC GGC GAA CTC GTT CCG GCG ACC    1241
Asp Glu Thr Arg Thr Phe Leu Glu Ala Gly Glu Leu Val Pro Ala Thr
        330                 335                 340

GAC TAC ATC AAG GCG CTG CGG GTG CGC ACC CTC ATC CAG GCA GCC TTC    1289
Asp Tyr Ile Lys Ala Leu Arg Val Arg Thr Leu Ile Gln Ala Ala Phe
345                 350                 355                 360

CGG GAA CTG TTC CAG GAC ATC GAT GTC CTG ATC GCA CCC ACG GTC AGC    1337
Arg Glu Leu Phe Gln Asp Ile Asp Val Leu Ile Ala Pro Thr Val Ser
                365                 370                 375

TCT CCG GCT CTG CCG CTC GAT GAC CTG GAA GTC ACT TGG CCC GAT GGC    1385
Ser Pro Ala Leu Pro Leu Asp Asp Leu Glu Val Thr Trp Pro Asp Gly
            380                 385                 390

ACA TCC GAA GGC GGC ACC ATC ACC TAT GTC CGT CTC AGC GCC CCC GGC    1433
Thr Ser Glu Gly Gly Thr Ile Thr Tyr Val Arg Leu Ser Ala Pro Gly
        395                 400                 405

AAC GTC ACC GGA CTT CCA GCG CTG TCG GTC CCC TCC GGC TTC ACC GAG    1481
Asn Val Thr Gly Leu Pro Ala Leu Ser Val Pro Ser Gly Phe Thr Glu
410                 415                 420

CAA GGC CTT CCC ACC GGT ATC CAG ATC ATC GGC CGT CCC TTC GAC GAG    1529
Gln Gly Leu Pro Thr Gly Ile Gln Ile Ile Gly Arg Pro Phe Asp Glu
425                 430                 435                 440
```

| | | | | | | | | | | | | | | | |
|---|---|---|---|---|---|---|---|---|---|---|---|---|---|---|---|
| GAG | ACC | GTC | CTC | AAC | GTC | GGT | CAC | GCC | TAC | GAA | GGC | TGC | ACG | GAC | TGG |
| Glu | Thr | Val | Leu | Asn | Val | Gly | His | Ala | Tyr | Glu | Gly | Cys | Thr | Asp | Trp |
| | | | | 445 | | | | | 450 | | | | | 455 | |

1577

| | | | | | | | | |
|---|---|---|---|---|---|---|---|---|
| CCG | CGA | CTG | GCG | CCG | CTT | TGAACTACTG | ACCCCCATTG | GAGAAAACCG |
| Pro | Arg | Leu | Ala | Pro | Leu | | | |
| | | | 460 | | | | | |

1625

AAGGAGAGAA CGATG                                                1640

( 2 ) INFORMATION FOR SEQ ID NO:13:

( i ) SEQUENCE CHARACTERISTICS:
        ( A ) LENGTH: 461 amino acids
        ( B ) TYPE: amino acid
        ( D ) TOPOLOGY: linear ( i i ) MOLECULE TYPE: protein ( x i ) SEQUENCE DESCRIPTION: SEQ ID NO:13:

| | | | | | | | | | | | | | | |
|---|---|---|---|---|---|---|---|---|---|---|---|---|---|---|
| Gly | Leu | His | Glu | Leu | Thr | Leu | Ala | Gln | Val | Ala | Ala | Lys | Ile | Glu | Asn |
| 1 | | | | 5 | | | | | 10 | | | | | 15 | |
| Lys | Glu | Leu | Ser | Pro | Val | Glu | Leu | Leu | Asp | Val | Ile | Leu | Ala | Arg | Val |
| | | | 20 | | | | | 25 | | | | | 30 | | |
| Ala | Glu | Ile | Glu | Pro | Lys | Ile | Ser | Ala | Phe | Val | Thr | Ile | Thr | Ala | Asp |
| | | | 35 | | | | 40 | | | | | 45 | | | |
| Ser | Ala | Arg | Lys | Ala | Ala | Arg | Leu | Ala | Ala | Asp | Glu | Ile | Ala | Gly | Gly |
| | 50 | | | | | 55 | | | | | 60 | | | | |
| His | Tyr | Arg | Gly | Pro | Leu | His | Gly | Val | Pro | Ile | Gly | Leu | Lys | Asp | Leu |
| 65 | | | | | 70 | | | | | 75 | | | | | 80 |
| Phe | Glu | Val | Ala | Gly | Val | Pro | Asn | Thr | Ala | Ser | Ser | Arg | Val | Arg | Ala |
| | | | | 85 | | | | | 90 | | | | | 95 | |
| Asp | Tyr | Ile | Pro | Ser | Ser | Asp | Gly | Ala | Val | Glu | Lys | Leu | Thr | Ala | |
| | | | 100 | | | | 105 | | | | | 110 | | | |
| Gly | Gly | Ala | Val | Met | Ile | Gly | Lys | Thr | His | Thr | His | Glu | Phe | Ala | Tyr |
| | | 115 | | | | | 120 | | | | | 125 | | | |
| Gly | Ala | Ile | Thr | Pro | Thr | Thr | Arg | Asn | Pro | Trp | Asp | Pro | Thr | Arg | Thr |
| | 130 | | | | | 135 | | | | | 140 | | | | |
| Pro | Gly | Gly | Ser | Ser | Gly | Gly | Thr | Ala | Ala | Leu | Ala | Ala | Gly | Leu | |
| 145 | | | | | 150 | | | | | 155 | | | | | 160 |
| Ile | Phe | Ala | Gly | Met | Gly | Thr | Asp | Thr | Gly | Ser | Ile | Arg | Ile | Pro | |
| | | | | 165 | | | | | 170 | | | | | 175 | |
| Ala | Ala | Val | Cys | Gly | Thr | Val | Gly | Leu | Lys | Pro | Thr | Tyr | Gly | Arg | Val |
| | | | 180 | | | | | 185 | | | | | 190 | | |
| Ser | Arg | Arg | Gly | Val | Thr | Ser | Leu | Ser | Trp | Ser | Leu | Asp | His | Ala | Gly |
| | | 195 | | | | | 200 | | | | | 205 | | | |
| Pro | Leu | Ala | Arg | Thr | Val | Glu | Asp | Ala | Ala | Ile | Met | Leu | Asn | Gln | Ile |
| | 210 | | | | | 215 | | | | | 220 | | | | |
| Ala | Gly | Tyr | Asp | Arg | Ala | Asp | Pro | Ala | Thr | Val | Asp | Val | Pro | Val | |
| 225 | | | | | 230 | | | | | 235 | | | | | 240 |
| Asp | Tyr | Ala | Ala | Ala | Leu | Thr | Gly | Asp | Val | Arg | Gly | Leu | Arg | Ile | Gly |
| | | | | 245 | | | | | 250 | | | | | 255 | |
| Val | Pro | Thr | Asn | Phe | Tyr | Thr | Asp | Asn | Val | His | Pro | Glu | Val | Ala | Ala |
| | | | 260 | | | | | 265 | | | | | 270 | | |
| Ala | Ala | Asp | Ala | Ala | Val | Ala | Gln | Leu | Ala | His | Leu | Gly | Ala | Val | Val |
| | | 275 | | | | | 280 | | | | | 285 | | | |
| Arg | Glu | Val | Lys | Ile | Pro | Met | Ala | Glu | Val | Ile | Val | Pro | Thr | Glu | Trp |
| | 290 | | | | | 295 | | | | | 300 | | | | |
| Ser | Leu | Leu | Val | Pro | Glu | Ala | Ser | Ala | Tyr | His | Gln | Gln | Met | Leu | Arg |
| 305 | | | | | 310 | | | | | 315 | | | | | 320 |

|  |  |  |  |  |  |  |  |  |  |  |  |  |  |  |
|---|---|---|---|---|---|---|---|---|---|---|---|---|---|---|
| Glu | Arg | Ala | Asp | His 325 | Tyr | Thr | Asp | Glu 330 | Thr | Arg | Thr | Phe | Leu 335 | Glu | Ala |
| Gly | Glu | Leu | Val 340 | Pro | Ala | Thr | Asp 345 | Tyr | Ile | Lys | Ala 350 | Leu | Arg | Val | Arg |
| Thr | Leu | Ile 355 | Gln | Ala | Ala | Phe 360 | Arg | Glu | Leu | Phe 365 | Gln | Asp | Ile | Asp | Val |
| Leu | Ile 370 | Ala | Pro | Thr | Val 375 | Ser | Pro | Ala | Leu 380 | Pro | Leu | Asp | Asp | Leu |
| Glu 385 | Val | Thr | Trp | Pro | Asp 390 | Gly | Thr | Ser | Glu 395 | Gly | Gly | Thr | Ile | Thr | Tyr 400 |
| Val | Arg | Leu | Ser | Ala 405 | Pro | Gly | Asn | Val | Thr 410 | Gly | Leu | Pro | Ala | Leu 415 | Ser |
| Val | Pro | Ser | Gly 420 | Phe | Thr | Glu | Gln 425 | Gly | Leu | Pro | Thr | Gly 430 | Ile | Gln | Ile |
| Ile | Gly | Arg 435 | Pro | Phe | Asp | Glu 440 | Thr | Val | Leu | Asn | Val 445 | Gly | His | Ala |
| Tyr | Glu 450 | Gly | Cys | Thr | Asp | Trp 455 | Pro | Arg | Leu | Ala | Pro 460 | Leu |

(2) INFORMATION FOR SEQ ID NO:14:

(i) SEQUENCE CHARACTERISTICS:
        (A) LENGTH: 144 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..144

(xi) SEQUENCE DESCRIPTION: SEQ ID NO:14:

| GGC | GGT | TCC | AGC | GGT | GGG | ACG | GCA | GCA | GCT | CTC | GCG | GCA | GGC | CTC | ATC | 48 |
|---|---|---|---|---|---|---|---|---|---|---|---|---|---|---|---|---|
| Gly 1 | Gly | Ser | Ser | Gly 5 | Gly | Thr | Ala | Ala | Ala 10 | Leu | Ala | Ala | Gly | Leu 15 | Ile |
| TTC | GCC | GGT | ATG | GGT | ACC | GAT | ACC | GGG | GGG | TCC | ATT | CGG | ATA | CCA | GCC | 96 |
| Phe | Ala | Gly | Met 20 | Gly | Thr | Asp | Thr | Gly 25 | Gly | Ser | Ile | Arg | Ile 30 | Pro | Ala |
| GCC | GTC | TGC | GGG | ACG | GTA | GGT | CTC | AAA | CCC | ACA | TAT | GGT | CGC | GTT | TCG | 144 |
| Ala | Val | Cys 35 | Gly | Thr | Val | Gly | Leu 40 | Lys | Pro | Thr | Tyr | Gly 45 | Arg | Val | Ser |

(2) INFORMATION FOR SEQ ID NO:15:

(i) SEQUENCE CHARACTERISTICS:
        (A) LENGTH: 48 amino acids
        (B) TYPE: amino acid
        (D) TOPOLOGY: linear (ii) MOLECULE TYPE: protein (xi) SEQUENCE DESCRIPTION: SEQ ID NO:15:

| Gly 1 | Gly | Ser | Ser | Gly 5 | Gly | Thr | Ala | Ala | Ala 10 | Leu | Ala | Ala | Gly | Leu 15 | Ile |
|---|---|---|---|---|---|---|---|---|---|---|---|---|---|---|---|
| Phe | Ala | Gly | Met 20 | Gly | Thr | Asp | Thr | Gly 25 | Gly | Ser | Ile | Arg | Ile 30 | Pro | Ala |
| Ala | Val | Cys 35 | Gly | Thr | Val | Gly | Leu 40 | Lys | Pro | Thr | Tyr | Gly 45 | Arg | Val | Ser |

(2) INFORMATION FOR SEQ ID NO:16:

(i) SEQUENCE CHARACTERISTICS:
        (A) LENGTH: 11 amino acids (B) TYPE: amino acid
(D) TOPOLOGY: linear (ii) MOLECULE TYPE: peptide (xi) SEQUENCE DESCRIPTION: SEQ ID NO:16:

Ala Thr Val Asp Val Pro Val Pro Asp Tyr Ala
1               5                   10

(2) INFORMATION FOR SEQ ID NO:17:

(i) SEQUENCE CHARACTERISTICS:
    (A) LENGTH: 32 base pairs
    (B) TYPE: nucleic acid
    (C) STRANDEDNESS: single
    (D) TOPOLOGY: linear (ii) MOLECULE TYPE: DNA (genomic)

(ix) FEATURE:
    (A) NAME/KEY: miscfeature
    (B) LOCATION: 3
    (D) OTHER INFORMATION: /note="N=inosine"

(ix) FEATURE:
    (A) NAME/KEY: miscfeature
    (B) LOCATION: 6
    (D) OTHER INFORMATION: /note="N=inosine."

(ix) FEATURE:
    (A) NAME/KEY: miscfeature
    (B) LOCATION: 9
    (D) OTHER INFORMATION: /note="N=inosine."

(ix) FEATURE:
    (A) NAME/KEY: miscfeature
    (B) LOCATION: 12
    (D) OTHER INFORMATION: /note="Y=C or T/U"

(ix) FEATURE:
    (A) NAME/KEY: miscfeature
    (B) LOCATION: 15
    (D) OTHER INFORMATION: /note="N=inosine"

(ix) FEATURE:
    (A) NAME/KEY: miscfeature
    (B) LOCATION: 18
    (D) OTHER INFORMATION: /note="N=inosine"

(ix) FEATURE:
    (A) NAME/KEY: miscfeature
    (B) LOCATION: 21
    (D) OTHER INFORMATION: /note="N=inosine"

(ix) FEATURE:
    (A) NAME/KEY: miscfeature
    (B) LOCATION: 24
    (D) OTHER INFORMATION: /note="N=inosine"

(ix) FEATURE:
    (A) NAME/KEY: miscfeature
    (B) LOCATION: 27
    (D) OTHER INFORMATION: /note="Y=C or T/U"

(ix) FEATURE:
    (A) NAME/KEY: miscfeature
    (B) LOCATION: 30
    (D) OTHER INFORMATION: /note="Y=C or T/U"

(xi) SEQUENCE DESCRIPTION: SEQ ID NO:17:

GCNACNGTNG AYGTNCCNGT NCCNGAYTAY GC                              32

(2) INFORMATION FOR SEQ ID NO:18:

(i) SEQUENCE CHARACTERISTICS:
    (A) LENGTH: 11 amino acids
    (B) TYPE: amino acid
    (D) TOPOLOGY: linear (i i) MOLECULE TYPE: peptide (x i) SEQUENCE DESCRIPTION: SEQ ID NO:18:

Glu Ala Gly Glu Leu Val Pro Ala Thr Asp Tyr
1               5                   10

(2) INFORMATION FOR SEQ ID NO:19:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (i i) MOLECULE TYPE: DNA (genomic)

(i x) FEATURE:
        (A) NAME/KEY: miscfeature
        (B) LOCATION: 3
        (D) OTHER INFORMATION: /note="R=A or G"

(i x) FEATURE:
        (A) NAME/KEY: miscfeature
        (B) LOCATION: 6
        (D) OTHER INFORMATION: /note="N=inosine"

(i x) FEATURE:
        (A) NAME/KEY: miscfeature
        (B) LOCATION: 9
        (D) OTHER INFORMATION: /note="N=inosine"

(i x) FEATURE:
        (A) NAME/KEY: miscfeature
        (B) LOCATION: 12
        (D) OTHER INFORMATION: /note="R=A or G"

(i x) FEATURE:
        (A) NAME/KEY: miscfeature
        (B) LOCATION: 13
        (D) OTHER INFORMATION: /note="Y=C or T/U"

(i x) FEATURE:
        (A) NAME/KEY: miscfeature
        (B) LOCATION: 15
        (D) OTHER INFORMATION: /note="N=inosine"

(i x) FEATURE:
        (A) NAME/KEY: miscfeature
        (B) LOCATION: 18
        (D) OTHER INFORMATION: /note="N=inosine"

(i x) FEATURE:
        (A) NAME/KEY: miscfeature
        (B) LOCATION: 21
        (D) OTHER INFORMATION: /note="N=inosine"

(i x) FEATURE:
        (A) NAME/KEY: miscfeature
        (B) LOCATION: 24
        (D) OTHER INFORMATION: /note="N=inosine"

(i x) FEATURE:
        (A) NAME/KEY: miscfeature
        (B) LOCATION: 27
        (D) OTHER INFORMATION: /note="N=inosine"

(i x) FEATURE:
        (A) NAME/KEY: miscfeature
        (B) LOCATION: 30
        (D) OTHER INFORMATION: /note="Y=C or T/U"

(x i) SEQUENCE DESCRIPTION: SEQ ID NO:19:

GARGCNGGNG ARYTNGTNCC NGCNACNGAY TA      32

(2) INFORMATION FOR SEQ ID NO:20:

(i) SEQUENCE CHARACTERISTICS:

(A) LENGTH: 32 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: miscfeature
(B) LOCATION: 3
(D) OTHER INFORMATION: /note="R=A or G"

(ix) FEATURE:
(A) NAME/KEY: miscfeature
(B) LOCATION: 6
(D) OTHER INFORMATION: /note="Y=C or T/U"

(ix) FEATURE:
(A) NAME/KEY: miscfeature
(B) LOCATION: 9
(D) OTHER INFORMATION: /note="N=inosine"

(ix) FEATURE:
(A) NAME/KEY: miscfeature
(B) LOCATION: 12
(D) OTHER INFORMATION: /note="Y=C or T/U"

(ix) FEATURE:
(A) NAME/KEY: miscfeature
(B) LOCATION: 15
(D) OTHER INFORMATION: /note="N=inosine"

(ix) FEATURE:
(A) NAME/KEY: miscfeature
(B) LOCATION: 18
(D) OTHER INFORMATION: /note="N=inosine"

(ix) FEATURE:
(A) NAME/KEY: miscfeature
(B) LOCATION: 21
(D) OTHER INFORMATION: /note="N=inosine"

(ix) FEATURE:
(A) NAME/KEY: miscfeature
(B) LOCATION: 24
(D) OTHER INFORMATION: /note="N=inosine"

(ix) FEATURE:
(A) NAME/KEY: miscfeature
(B) LOCATION: 27
(D) OTHER INFORMATION: /note="N=inosine"

(ix) FEATURE:
(A) NAME/KEY: miscfeature
(B) LOCATION: 30
(D) OTHER INFORMATION: /note="N=inosine"

(ix) FEATURE:
(A) NAME/KEY: miscfeature
(B) LOCATION: 16
(D) OTHER INFORMATION: /note="Y=C or T/U"

(xi) SEQUENCE DESCRIPTION: SEQ ID NO:20:

CARGAYATNG AYGTNYTNAT NGCNCCNACN GT  32

(2) INFORMATION FOR SEQ ID NO:21:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: miscfeature
(B) LOCATION: 7
(D) OTHER INFORMATION: /note="V=A, C or G."

-continued (ix) FEATURE:
  (A) NAME/KEY: miscfeature
  (B) LOCATION: 10
  (D) OTHER INFORMATION: /note="S=C or G."

(ix) FEATURE:
  (A) NAME/KEY: miscfeature
  (B) LOCATION: 13
  (D) OTHER INFORMATION: /note="W=A or T/U."

(ix) FEATURE:
  (A) NAME/KEY: miscfeature
  (B) LOCATION: 16
  (D) OTHER INFORMATION: /note="B=C or G or T/U."

(ix) FEATURE:
  (A) NAME/KEY: miscfeature
  (B) LOCATION: 19
  (D) OTHER INFORMATION: /note="W=A or T/U."

(ix) FEATURE:
  (A) NAME/KEY: miscfeature
  (B) LOCATION: 1..23
  (D) OTHER INFORMATION: /note="Nucleotides 1-23 of both
    the 5-3 and 3-5 strands were used to prime
    amplification of genomic DNA at 45 degrees C."

(xi) SEQUENCE DESCRIPTION: SEQ ID NO:21:

AAGCTTVCTS TTWTGBCAWG CGT					23

(2) INFORMATION FOR SEQ ID NO:22:

(i) SEQUENCE CHARACTERISTICS:
    (A) LENGTH: 23 base pairs
    (B) TYPE: nucleic acid
    (C) STRANDEDNESS: single
    (D) TOPOLOGY: linear (ii) MOLECULE TYPE: DNA (genomic)

(ix) FEATURE:
    (A) NAME/KEY: miscfeature
    (B) LOCATION: 7
    (D) OTHER INFORMATION: /note="V=A, C or G."

(ix) FEATURE:
    (A) NAME/KEY: miscfeature
    (B) LOCATION: 19
    (D) OTHER INFORMATION: /note="W=A or T/U."

(ix) FEATURE:
    (A) NAME/KEY: miscfeature
    (B) LOCATION: 1..23
    (D) OTHER INFORMATION: /note="Nucleotides 1-23 of both
      the 5-3 and 3-5 strands were used to prime
      amplification of genomic DNA at 48 degrees C."

(xi) SEQUENCE DESCRIPTION: SEQ ID NO:22:

AAGCTTVCTG TTTTGTCAWG CGT					23

(2) INFORMATION FOR SEQ ID NO:23:

(i) SEQUENCE CHARACTERISTICS:
    (A) LENGTH: 24 base pairs
    (B) TYPE: nucleic acid
    (C) STRANDEDNESS: single
    (D) TOPOLOGY: linear (ii) MOLECULE TYPE: DNA (genomic)

(ix) FEATURE:
    (A) NAME/KEY: miscfeature
    (B) LOCATION: 2
    (D) OTHER INFORMATION: /note="D=A or G or T/U; not C."

(ix) FEATURE:
    (A) NAME/KEY: miscfeature
    (B) LOCATION: 5

(D) OTHER INFORMATION: /note="S=C or G."

( i x ) FEATURE:
 (A) NAME/KEY: miscfeature
 (B) LOCATION: 8
 (D) OTHER INFORMATION: /note="S=C or G."

( i x ) FEATURE:
 (A) NAME/KEY: miscfeature
 (B) LOCATION: 10
 (D) OTHER INFORMATION: /note="M=A or C."

( i x ) FEATURE:
 (A) NAME/KEY: miscfeature
 (B) LOCATION: 11
 (D) OTHER INFORMATION: /note="H=A or c or T/U; not G."

( i x ) FEATURE:
 (A) NAME/KEY: miscfeature
 (B) LOCATION: 12
 (D) OTHER INFORMATION: /note="W=A or T/U."

( i x ) FEATURE:
 (A) NAME/KEY: miscfeature
 (B) LOCATION: 13
 (D) OTHER INFORMATION: /note="R=A or G."

( i x ) FEATURE:
 (A) NAME/KEY: miscfeature
 (B) LOCATION: 1..24
 (D) OTHER INFORMATION: /note="Oligonucleotide to be used at 45 degrees C."

( i x ) FEATURE:
 (A) NAME/KEY: CDS
 (B) LOCATION: 1..18

( x i ) SEQUENCE DESCRIPTION: SEQ ID NO:23:

GDCTSGTSGM HWRGTATCGA ATTC      24

(2) INFORMATION FOR SEQ ID NO:24:

( i ) SEQUENCE CHARACTERISTICS:
  (A) LENGTH: 24 base pairs
  (B) TYPE: nucleic acid
  (C) STRANDEDNESS: single
  (D) TOPOLOGY: linear ( i i ) MOLECULE TYPE: DNA (genomic)

( i x ) FEATURE:
  (A) NAME/KEY: miscfeature
  (B) LOCATION: 2
  (D) OTHER INFORMATION: /note="K=G or T/U."

( i x ) FEATURE:
  (A) NAME/KEY: miscfeature
  (B) LOCATION: 5
  (D) OTHER INFORMATION: /note="R=A, G."

( i x ) FEATURE:
  (A) NAME/KEY: miscfeature
  (B) LOCATION: 8
  (D) OTHER INFORMATION: /note="S=C, G."

( i x ) FEATURE:
  (A) NAME/KEY: miscfeature
  (B) LOCATION: 12
  (D) OTHER INFORMATION: /note="Y=C or T/U."

( i x ) FEATURE:
  (A) NAME/KEY: miscfeature
  (B) LOCATION: 16
  (D) OTHER INFORMATION: /note="R=A, G."

( i x ) FEATURE:
  (A) NAME/KEY: miscfeature
  (B) LOCATION: 1..23
  (D) OTHER INFORMATION: /note="Oligonucleotide to be used at 48 degrees C."

( i x ) FEATURE:
(A) NAME/KEY: CDS
(B) LOCATION: 1..18

( x i ) SEQUENCE DESCRIPTION: SEQ ID NO:24:

GKCTRGTSGA AYGGTRTCGA ATTC 24

What is claimed is:

1. A process for the synthesis of ammonium adipate by the hydrolysis of adipamide or ammonium adipamate comprising:
   (a) contacting said adipamide or ammonium adipamate under conditions wherein said synthesis will occur with a polypeptide coded for by a DNA sequence selected from the group consisting of:
   the sequence coding for the amidase of *Brevibacterium* R 312 shown in FIG. 9 (SEQ. ID NO: 10), the sequence shown in FIG. 14 (SEQ. ID NO:12), an analog of these sequences resulting from the degeneracy of the genetic code, and
   a DNA hybridizing with one of these sequences or with a fragment thereof and coding for a polypeptide having amidase activity; or
   (b) contacting said adipamide or ammonium adipamate under conditions wherein said synthesis will occur with a recombinant microorganism which produces said polypeptide.

2. A process according to claim 1 wherein the host microorganism is an enterobacterium.

3. A process according to claim 2 wherein the enterobacterium is *E. coli*.

4. A process according to claim 1 wherein the host microorganisum is a corynebacterium.

5. A process according to claim 4 wherein this bacterium belongs to the genera *Corynebacterium, Brevibacterium* or *Rhodococcus*.

6. A process according to any one of the preceding claims wherein the polypeptide or the recombinant microorganism is immobilized on or in a solid support.

* * * * *